(12) United States Patent
Mishima et al.

(10) Patent No.: US 7,204,830 B2
(45) Date of Patent: Apr. 17, 2007

(54) DISPOSABLE ABSORBENT ARTICLE WITH STANDING BARRIER CUFFS, POCKET, AND FOLDING GUIDES FOR SEPARATING FECES FROM URINE

(75) Inventors: Yoshitaka Mishima, Mitoyo-gun (JP); Kaiyo Nakajima, Mitoyo-gun (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/103,516

(22) Filed: Apr. 12, 2005

(65) Prior Publication Data

US 2005/0228358 A1  Oct. 13, 2005

(30) Foreign Application Priority Data

Apr. 12, 2004  (JP) ............................. 2004-116749

(51) Int. Cl.
 A61F 13/495 (2006.01)
 A61F 13/537 (2006.01)
(52) U.S. Cl. ........................... 604/385.19; 604/385.201
(58) Field of Classification Search ........... 604/385.28, 604/385.19, 385.24–385.29, 385.101, 358, 604/385.01
See application file for complete search history.

(56) References Cited

U.S. PATENT DOCUMENTS

| | | | | |
|---|---|---|---|---|
| 5,558,661 | A * | 9/1996 | Roe et al. ............... | 604/385.19 |
| 6,165,160 | A * | 12/2000 | Suzuki et al. .......... | 604/385.201 |
| 6,248,098 | B1 * | 6/2001 | Sayama .................. | 604/385.28 |
| 6,406,465 | B1 * | 6/2002 | Otsubo .................. | 604/385.01 |
| 6,464,676 | B2 * | 10/2002 | Mishima ................ | 604/385.19 |
| 6,527,756 | B1 * | 3/2003 | Mishima et al. ....... | 604/385.19 |
| 6,638,260 | B2 * | 10/2003 | Mishima ................ | 604/385.01 |
| 6,638,262 | B2 * | 10/2003 | Suzuki et al. .......... | 604/385.28 |
| 6,921,394 | B2 * | 7/2005 | Sayama et al. ........ | 604/385.19 |

(Continued)

FOREIGN PATENT DOCUMENTS

EP  0955028 A2 * 11/1999

(Continued)

OTHER PUBLICATIONS

Kazuaki et al., Throw-Away Diaper, Aug. 6, 1996, JP 08-196565 patent abstract only.*

Primary Examiner—Tatyana Zalukaeva
Assistant Examiner—Laura C. Hill
(74) Attorney, Agent, or Firm—Lowe Hauptman & Berner LLP

(57) ABSTRACT

A disposable wearing article includes a liquid-impervious chassis, a pair of liquid-impervious leak-barrier sheets laid along transversely opposite side edges of the chassis, a body fluid absorbent first panel extending over a crotch region and a rear waist region of the chassis and joined to the chassis, and a body fluid absorbent second panel extending over a front waist region and the crotch region. The second panel has a front portion joined to the front waist region, a distal portion and transversely opposite side edges joined to the chassis. The distal portion has side sections extending upward above the chassis and joined to distal sections of the respective leak-barrier sheets, and a transversely middle section which extends between the side sections and is convex upward above the side sections and thereby a pocket opening from the crotch region toward the rear waist region is formed between the chassis and the distal portion.

8 Claims, 16 Drawing Sheets

U.S. PATENT DOCUMENTS

| | | | |
|---|---|---|---|
| 7,033,341 B2 * | 4/2006 | Mishima | 604/385.01 |
| 2001/0016719 A1 * | 8/2001 | Mishima | 604/385.19 |
| 2002/0077615 A1 * | 6/2002 | Mishima | 604/385.01 |

FOREIGN PATENT DOCUMENTS

| | | |
|---|---|---|
| EP | 1 114 631 A2 | 7/2001 |
| EP | 1 234 563 A3 | 8/2002 |
| EP | 1 323 339 A2 | 7/2003 |
| EP | 1 224 922 A3 | 6/2004 |
| EP | 1 234 563 A3 | 6/2004 |
| JP | 8-196565 | 8/1996 |
| JP | 1996-196565 | 8/1996 |
| JP | 2003-325563 | 11/2003 |

* cited by examiner

DISPOSABLE ABSORBENT ARTICLE WITH STANDING BARRIER CUFFS, POCKET, AND FOLDING GUIDES FOR SEPARATING FECES FROM URINE

RELATED APPLICATIONS

The present application is based on, and claims priority from, Japanese Application Number 2004-116749, filed Apr. 12, 2004, the disclosure of which is hereby incorporated by reference herein in its entirety.

BACKGROUND OF THE INVENTION

The present invention relates to a disposable wearing article adapted for absorption and retention of bodily wastes.

There has already been proposed a disposable diaper having a front waist region, a rear waist region and a crotch region extending between these waist regions and comprising a liquid-pervious topsheet facing the wearer, a liquid-impervious backsheet facing away from the wearer and a liquid-absorbent core interposed between these top- and backsheets and extending between the front and rear waist regions. The core consists of an upper layer core and a lower layer core overlapping each other in a thickness direction of the diaper. Such a diaper is disclosed, for example, in Japanese Unexamined Patent Application Publication No. 1996-196565 (hereinafter referred to as "Citation").

The upper layer core comprises, in turn, a front core extending from the front waist region into the crotch region and a rear core extending from the crotch region into the rear waist region. Ends of the front and rear cores facing each other are spaced in a back-and-forth direction by a predetermined dimension. Between these ends of the front and rear cores facing each other, the lower layer core covered with the topsheet is exposed. The topsheet covering the upper surface of the upper layer core are folded downward toward the lower layer core along the respective ends of the front and rear cores facing each other and folded into a spaced defined between the upper layer core and the lower layer core. In this diaper of prior art, difference in level between is defined between the front and rear cores, i.e., the upper layer core and the lower layer core in the crotch region so that the ends of the front and rear cores facing each other may cooperate with the lower layer core to form a pocket depressed in a thickness direction of the diaper.

In the case of the diaper disclosed in Citation, however, respective lower surfaces of the front and rear cores readily come in contact with the upper surface of the lower layer core and it is difficult for this known diaper to form a desired space between the front core and the lower layer core as sell as to form a desired space between the rear core and the lower layer core. Even if bodily wastes moves into the pocket formed in the crotch region, body wastes can not be properly received between the front core and the lower layer core as well as between the rear core and the lower layer core. Even if a limited space is formed between the front and rear cores and the lower layer core, it is impossible for such limited space to accommodate a large amount of bodily waste which rather spreads over the upper surfaces of the front and rear cores and/or the lower layer core. Consequently, urine and feces of bodily wastes may be mixed with each other and the wearer's skin may be contaminated with such a mixture. Furthermore, the upper layer core and the lower layer core are placed upon each other in the front and rear waist regions and thickness dimensions of the core in the front and rear waist regions are unacceptably increased to make the core bulky in these waist regions. Such a bulkiness may create a feeling of discomfort against the wearer.

SUMMARY OF THE INVENTION

It is an object of the present invention to provide a disposable wearing article improved so that the crotch region can be formed with a pocket adapted to receive feces without being mixed with urine, on one hand, and the wearer can be free from a feeling of discomfort due to local bulkiness of the core, on the other hand.

According to the present invention, there is provided a disposable wearing article comprising a liquid-impervious chassis having a front waist region, a rear waist region, a crotch region, a pair of liquid-impervious leak-barrier sheets laid on transversely opposite side edges of the chassis, a body fluid absorbent first panel laid between the pair of leak-barrier sheets and joined to the chassis wherein the leak-barrier sheets respectively have proximal lateral sections extending in the longitudinal direction along the side edges of the chassis, distal sections provided with stretchable elastic members extending in the longitudinal direction and contractibly attached thereto so that the distal sections are normally biased to rise above the chassis and longitudinally opposite ends respectively laid on front and rear ends of the chassis and collapsed in the transverse direction.

The article further comprises a body fluid absorbent second panel laid between the pair of leak-barrier sheets and extending over the rear waist region as well as the crotch region of the chassis, the first panel extending over the crotch region as well as the rear waist region of the chassis, and the second panel having a proximal front portion joined to the front waist region of the chassis at least along the front end thereof, a distal portion extending in the crotch region and transversely opposite side edges extending along the side edges of the chassis and the distal portion of the second panel having a pair of side sections extending upward from the side edges of the chassis and joined to the distal sections of the leak-barrier sheets and a transversely middle section extending between the side sections so as to be convex upward above the side sections, the middle section at least partially extending upward beyond upper ends of the distal sections of the respective leak-barrier sheets so that the chassis cooperates with the distal portion of the second panel to form a pocket adapted to open in the front waist region and the crotch region or at least in the crotch region.

The present invention may include the following preferred embodiments.

A distal edge of the distal portion is folded upward above the second panel so that the distal edge extends upward beyond the distal edges of the leak-barrier sheets.

A thickness dimension of at least the middle section of distal edge of the second panel is larger than a thickness dimension of the distal portion except for the distal edge and wherein the middle section extends upward beyond the distal edge of the distal sections of the leak-barrier sheets.

The side sections of the distal portion are joined to the distal sections of the leak-barrier sheets at a level lower than the distal edges so that distal edges of the leak-barrier sheets extend upward above the side sections.

The pocket is provided with a spacer extending in the transverse direction and having transversely opposite ends joined to at least one of the side sections and the transversely opposite side edges of the distal portion and an intermediate section defined between the transversely opposite ends, and the side sections of the distal portion are drawn by the spacer inward as viewed in the transverse direction of the chassis.

The spacer is elastically stretchable in the transverse direction and contractibly attached to the pocket so that the side sections of the distal portion are drawn inward as viewed in the transverse direction of the chassis under contractile force of the spacer.

A pair of folding guides spaced apart from each other by a predetermined dimension in the transverse direction and extending in the longitudinal direction are formed between the side sections and the middle section in the distal portion of the second panel.

The folding guides extend to the transversely opposite side edges on the side of the front portion so that a distance between the folding guides gradually increases from the distal edge of the distal portion toward the front portion.

The side sections of the distal portion are joined to the distal sections of the respective leak-barrier sheets in the vicinity of the folding guides.

The second panel presents a stiffness lower along the folding guides than in the distal portion of the second panel except for the folding guides.

The second panel presents a stiffness being higher along the folding guides than in the distal portion of the second panel except for the folding guides.

The first panel extends over the rear waist region and a generally rear half of the crotch region of the chassis while the second panel extends over the front waist region and a generally front half of the crotch region of the chassis and wherein a front end of the first panel underlies the distal portion of the second panel and extends into the pocket.

The first panel comprises a liquid-pervious first sheet and a liquid-pervious second sheet underlying the liquid-pervious first sheet while the second panel comprises a liquid-pervious second sheet and a liquid-absorbent second core wrapped with the second sheet.

With the article according to the present invention, the distal portion of the second panel rises in an upward convex circular arc above the chassis and the pocket opening at least in the crotch region is formed between the chassis and the distal portion. In this way, the pocket reliably receives feces if feces discharged onto the rear half of the crotch region and the rear waist region moves toward the front waist region. Urine discharged onto the front waist region and the crotch region is absorbed and contained by the second panel while feces discharged onto the crotch region and the rear waist region is absorbed and contained by the first panel and then received by the pocket. In this way, urine and feces are separated from each other and thus the wearer's skin is reliably protected from being contaminated with a mixture of urine and feces. The side sections of the distal portion of the second panel are joined to the distal sections of the respective leak-barrier sheets and thereby the distal portion is held up above the chassis by the distal sections so that the distal portion may be kept by the distal sections in an upward convex shape and the side sections extending upward above the chassis may be protected being unintentionally collapsed. Consequently, the pocket is hardly closed and reliably receives feces. The transversely middle section of the distal portion extends above the distal edges of the distal sections of the leak-barrier sheets so that the transversely middle section is in close contact with an intermediate region defined between the genital organ and the anus of the wearer and thereby forms the barrier adapted to divide the genital organ and the anus off from each other. As a result, urine and feces can be reliably separated from each other and thereby the wearer's skin can be reliably protected from contaminated with mixture of urine and feces. Furthermore it is unlikely that the first and second panels might overlap each other in the front and rear waist regions to make these panels locally bulky and the wearer of the article might suffer from a feeling of discomfort.

With the embodiment of the invention wherein the distal edge is folded upward above the second panel and the middle section of the distal edge folded in this manner extends upward beyond the distal edges of the distal section of the respective leak-barrier sheets, the middle section of the distal edge reliably comes in close contact with the intermediate region between the genital organ and the anus of the wearer and forms the barrier adapted to divide the genital organ and the anus off from each other. This barrier reliably divides urine and feces off from each other and reliably protects the wearer's skin from contamination due to urine and feces commingled together.

With the embodiment of the invention wherein a thickness dimension of the side sections of the distal portion is larger than a thickness dimension of the distal portion except for the distal edge of the distal edge extends upward beyond the distal edge of the distal sections of the respective leak-barrier sheets, the middle section of the distal edge reliably comes in close contact with the intermediate region between the genital organ and the anus of the wearer and forms the barrier adapted to divide the genital organ and the anus off from each other. This barrier reliably divides urine and feces off from each other and reliably protects the wearer's skin from contamination due to urine and feces commingled together.

With the embodiment of the invention wherein the side sections of the distal portion are joined to the distal sections of the leak-barrier sheets at the level lower than the distal edges so that the distal edges of the leak-barrier sheets extend upward above the side sections, the distal edges stand in the way of urine spreading on the upper surface of the distal portion and prevent urine from leaking sideways beyond the distal portion.

With the embodiment of the invention wherein the pocket is provided with the spacer extending in the transverse direction and the side sections of the distal portion of the second panel are drawn by the spacer inward as viewed in the transverse direction of the chassis, the shape of the distal portion is kept by the spacer convex upward above the chassis and it is unlikely that the side sections extending upward above the chassis might be unintentionally collapsed. In this way, the spacer can be effectively utilized to reliably keep the shape of the pocket formed between the chassis and the distal portions of the second panel. The pocket is hard to be closed and can reliably receive feces.

With the embodiment of the invention wherein the spacer is elastically stretchable in the transverse direction and contractibly attached to the pocket so that the side sections of the distal portion are drawn inward as viewed in the transverse direction of the chassis under contractile force of the spacer, the shape of the distal portion is kept by the spacer convex upward above the chassis and it is unlikely that the side sections extending upward above the chassis might be unintentionally collapsed. In this way, the spacer can be effectively utilized to reliably keep the shape of the pocket formed between the chassis and the distal portions of the second panel. The pocket is hard to be closed and can reliably receive feces.

With the embodiment of the invention wherein a pair of folding guides spaced from each other by a predetermined dimension in the transverse direction and extending in the longitudinal direction are formed between the side sections and the middle section in the distal portion of the second panel, the distal portion of the second panel are folded along the folding guides and thereby the distal portion is clearly defined into the side sections lying outside the respective folding guides and the transversely middle section extending between the folding guides. Such feature facilitates the side sections to rise above the chassis and at the same time facilitates the distal portion to become convex upward above the chassis. Thus the pocket is reliably formed between the chassis and the distal portion.

With the embodiment of the invention wherein a distance between the folding guides gradually increases from the distal edge of the distal portion toward the front portion and these folding guides extend to the transversely opposite side edges, the distal portion of the second panel are folded along the folding guides and thereby the distal portion is clearly defined into the side sections lying outside the respective folding guides and the transversely middle section extending between the folding guides. Such feature facilitates the side sections to rise above the chassis and at the same time facilitates the distal portion to become convex upward above the chassis. Thus the pocket is reliably formed between the chassis and the distal portion.

With the embodiment of the invention the side sections constituting the distal portion of the second panel are joined to the distal sections of the respective leak-barrier sheets in the vicinity of the respective folding guides so that the distal portion are folded along the folding guides as the respective distal sections raise the distal portion above the chassis. In this way, the distal portion is reliably folded along the respective folding guides, facilitating the side sections to rise above the chassis and thereby facilitating the distal portion to become convex upward above the chassis so that the pocket can be reliably formed between the chassis and the distal portion of the second panel.

With the embodiment of the invention wherein the second panel has a stiffness lower along the folding guides than in the distal portion of the second panel except for the folding guides, the distal portion can be reliably folded along the folding guides and thereby the distal portion of the second panel can easily become convex upward above the chassis. In this way, the pocket can be reliably formed between the chassis and the distal portion of the second panel.

With the embodiment of the invention wherein the second panel has a stiffness higher along the folding guides than in the distal portion of the second panel except for the folding guides, the distal portion can be reliably folded on both sides of each of the folding guides and thereby the distal portion of the second panel can easily become convex upward above the chassis. In this way, the pocket can be reliably formed between the chassis and the distal portion of the second panel.

With the embodiment of the invention wherein the first panel extends over the rear waist region and a generally rear half of the chassis while the second panel extends over the front waist region and a generally front half of the crotch region of the chassis and wherein the front end of the first panel underlies the distal portion of the second panel and extends into the pocket, the pocket is formed in a generally front half of the crotch region so that urine discharged onto the front half of the crotch region can be absorbed and contained by the second panel while feces discharged on the rear half of the crotch region can be absorbed and contained by the first panel and received by the pocket. In this article, the distal portion of the second panel comes in contact with the intermediate region between the genital organ and the anus of the wearer so that urine and feces can be reliably separated from each other and the wearer's skin can be reliably protected from contamination with a mixture of urine and feces. Even if urine leaks through the second panel into the pocket, such urine can be absorbed and contained together with feces by the first panel and it is likely that urine and feces might be mixed together within the pocket.

With the embodiment of the invention wherein the first panel comprises a liquid-pervious first sheet and a liquid-absorbent first core underlying the first sheet while the second panel comprises a liquid-pervious second sheet and a liquid-absorbent second core wrapped with the second sheet, urine is absorbed and retained by the second core while feces is absorbed and retained by the first core. In this way, it is unlikely that urine and feces might leak from the first and second panels.

DETAILED DESCRIPTION OF THE PREFERRED EMBODIMENTS

Details of the disposable wearing article according to the present invention will be more fully understood from the description of a typical embodiment given hereunder with reference to the accompanying drawings.

Figure 1:
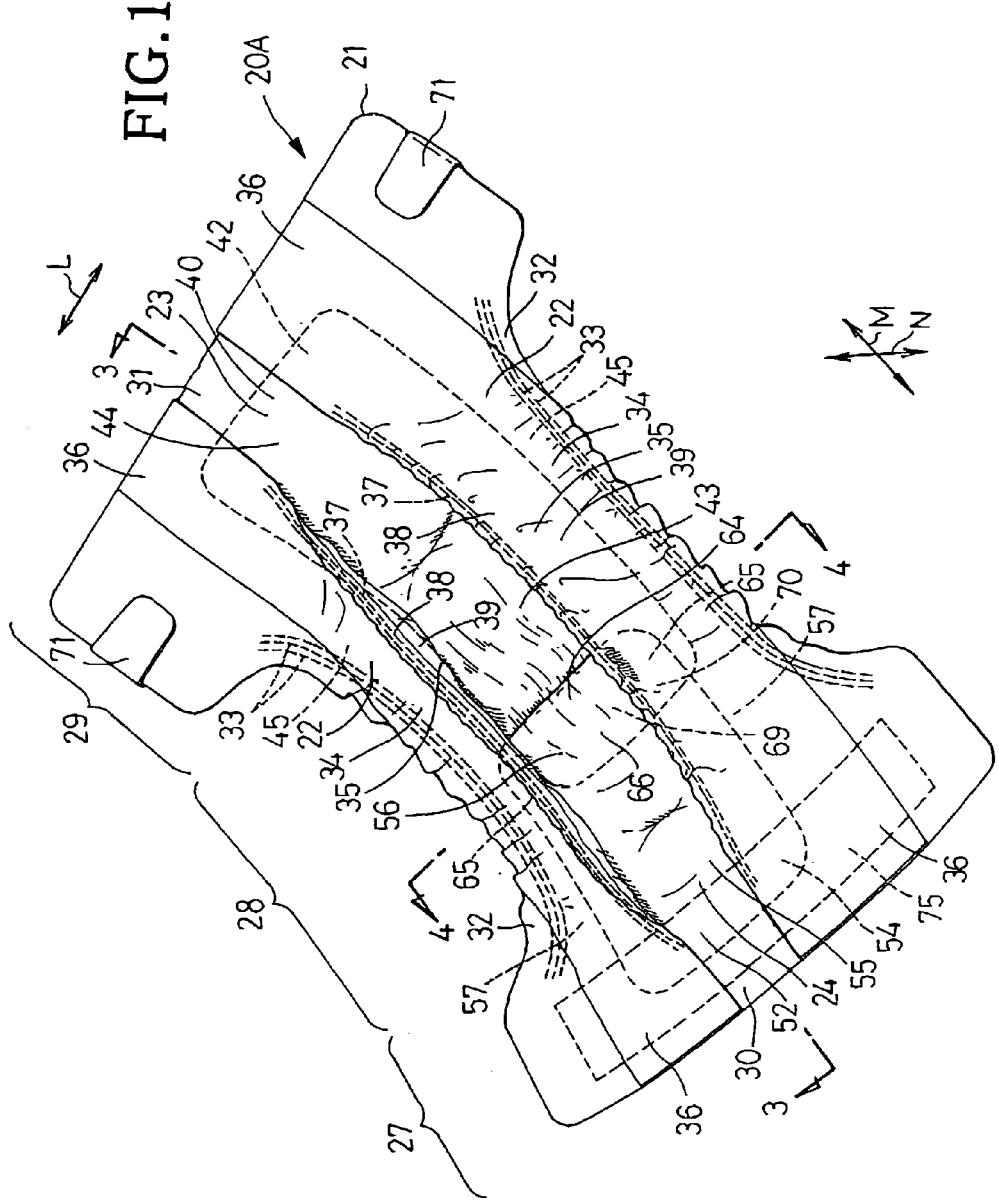
FIG. 1 is a perspective view showing a disposable wearing article according to a typical embodiment of the invention.
Figure 2:
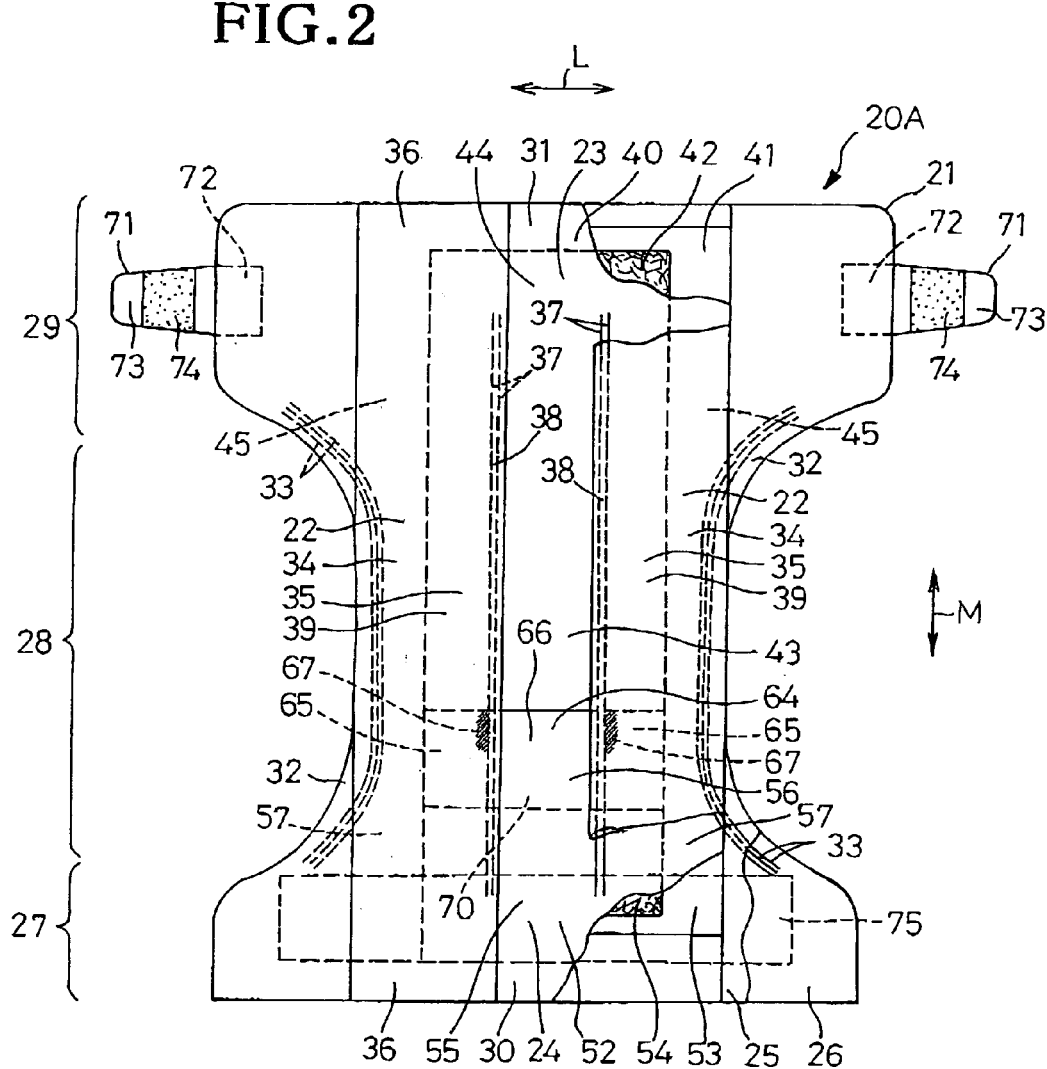
FIG. 2 is a partially cutaway plan view showing the wearing article of FIG. 1 as viewed from the side of the panel.
Figure 3:
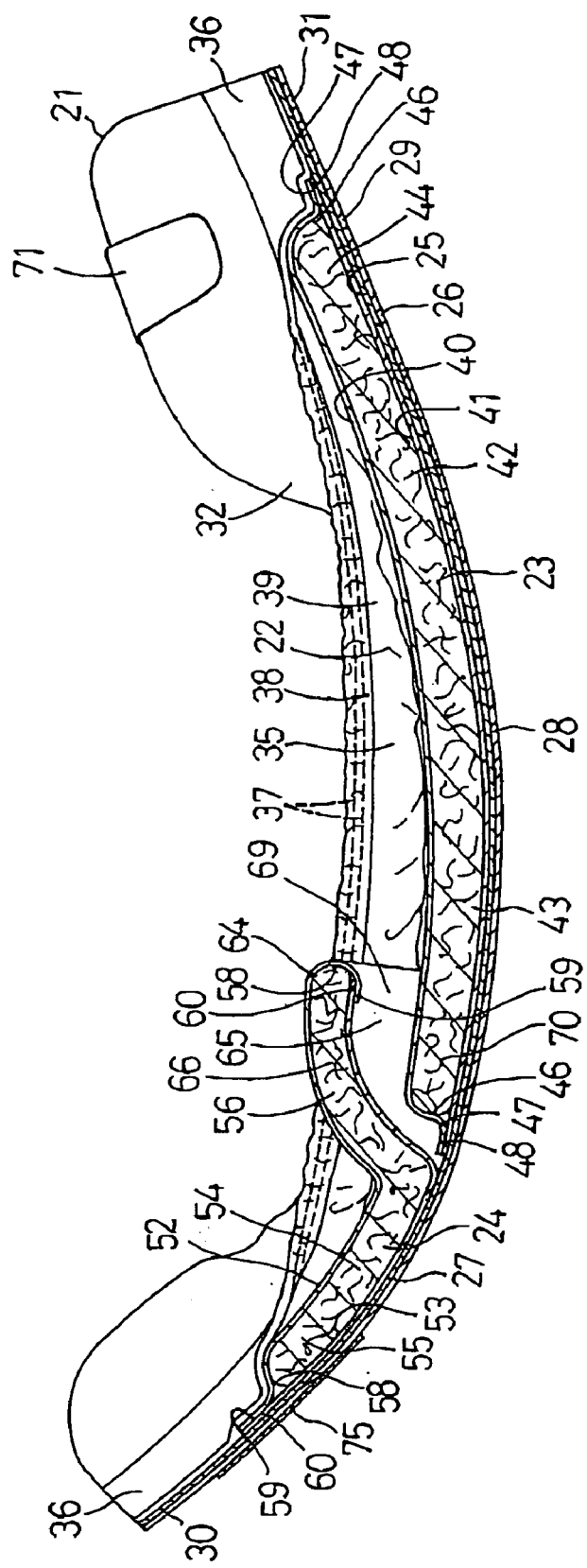
FIG. 3 is a sectional view taken along the line 3—3 in FIG. 1.
Figure 4:
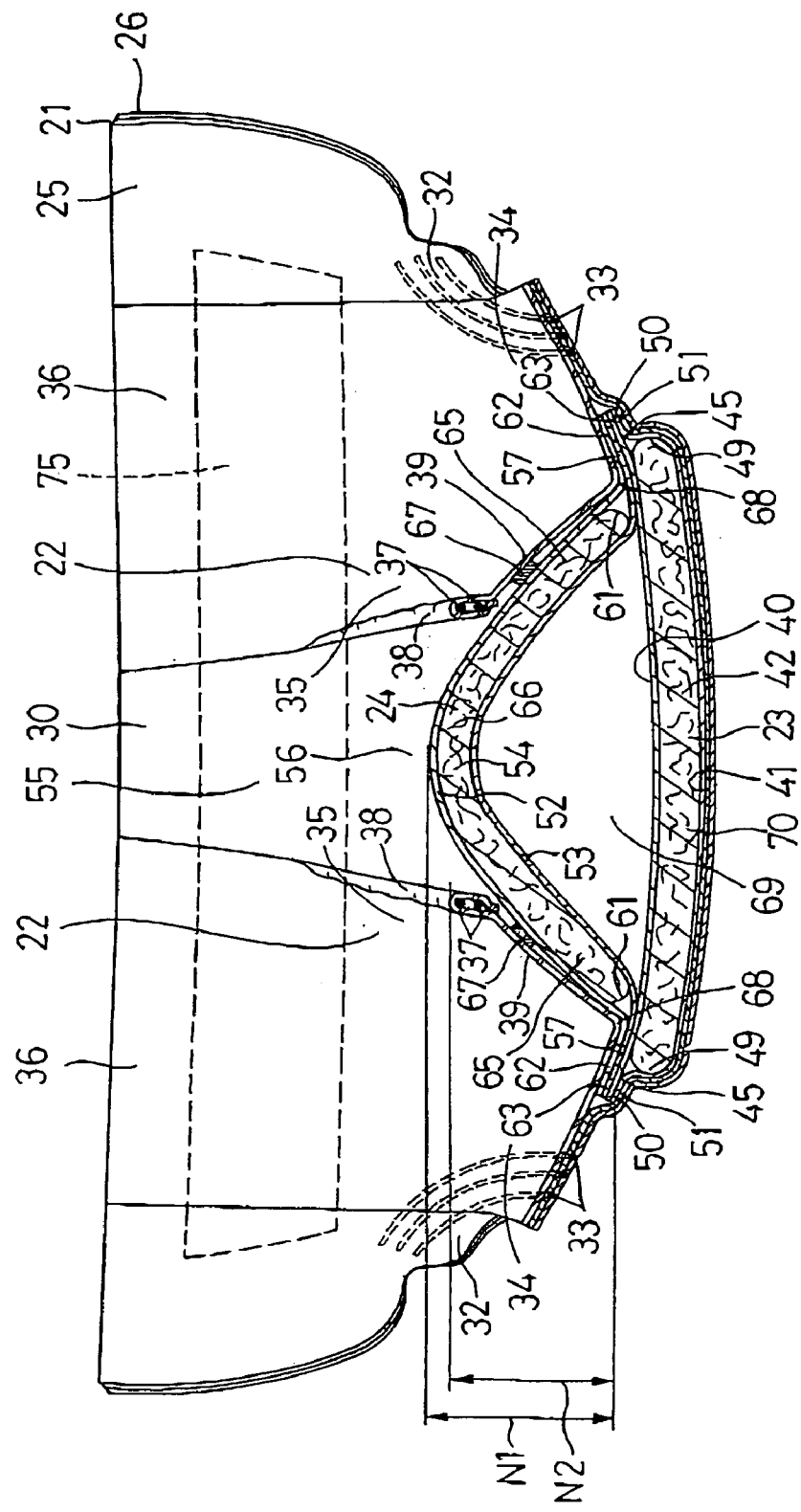
FIG. 4 is a sectional view taken along the line 4—4 in FIG. 1.

FIG. 1 is a perspective view showing a disposable wearing article 20A to a typical embodiment of the invention, FIG. 2 is a partially cutaway plan view showing the article 20A of FIG. 1 as viewed from the side of first and second panels 23, 24. FIG. 3 is a sectional view taken along a line 3—3 in FIG. 1 and FIG. 4 is a sectional view taken along a line 4—4 in FIG. 1. In FIGS. 1 and 2, a transverse direction is indicated by an arrow L, a longitudinal direction is indicated by an arrow M and a thickness direction is indicated by an arrow N (in FIG. 1 alone) FIG. 2 shows the article 20A as developed against a contractile force of elastic members 33, 37 in the longitudinal direction as well as in the transverse direction.

The article 20A comprises a liquid-impervious chassis 21, a pair of liquid-impervious leak-barrier sheets 22 extending in the longitudinal direction on the inner side of the chassis 21, and first and second body fluid absorbent panels 23, 24 laid back and forth in the longitudinal direction on the inner side of the chassis.

The chassis 21 is formed of a composite sheet consisting of a pair of hydrophobic fibrous nonwoven fabric layers 25, 26 laminated together wherein mutually opposed surfaces of nonwoven fabric layers 25, 26 are joined to each other. The chassis 21 defines, in the longitudinal direction, a front waist region 27, a rear waist region 29 and a crotch region 28 extending between these waist regions 27, 29. The chassis 21 further is contoured by front and rear ends 30, 31 respectively extending across the front and rear waist regions 27, 29 and in the transverse direction and transversely opposite lateral sections 32 extending in the longitudinal direction between the front and rear waist regions 27, 29. In the crotch region 28, these lateral sections 32 describe circular arcs which are convex inward as viewed in the transverse direction to form the article 20A into a generally hourglass-like shape. A plurality of leg-surrounding elastic members 33 extending along the lateral sections 32 of the crotch region 28 are contractibly attached to the chassis 21. The leg-surrounding elastic members 33 are interposed between the nonwoven fabric layers 25, 26 and joined to mutually opposed surfaces of these layers 25, 26 while the elastic members 33 are stretched at a predetermined ratio in the longitudinal direction.

The leak-barrier sheets 22 are laid on the respective lateral sections 32 of the chassis 21 and comprise proximal lateral sections 34 extending in the longitudinal direction, distal sections 35 extending in parallel to the proximal lateral sections 34 and normally biased to rise above the chassis 21, and longitudinally opposite ends 36 laid on the front and rear end zones 30, 31, respectively and collapsed inward as viewed in the transverse direction of the chassis 21. The proximal lateral sections 34 and the distal sections 35 extend between the front and rear end zones 30, 31 of the chassis 21. The distal sections 35 respectively have distal edges 38 along which stretchable elastic members 37 extending in the longitudinal direction are contractibly attached to the leak-barrier sheets 24 and an intermediate section 39 respectively extending from the proximal lateral sections 34 to the distal edges 38. The elastic members 37 are secured to the respective distal edges 38 while these elastic members 37 are stretched at a predetermined ratio in the longitudinal direction. As the article 20A is curved with the inner surface of the chassis 21 inside and the elastic members 37 contract, the distal edges 38 correspondingly contract in the longitudinal direction and the distal section 35 rises above the chassis 21 to form a pair of barriers against bodily wastes.

The first panel 23 is shaped in a rectangle which is relatively long in the longitudinal direction and laid between respective distal sections 63 of the leak-barrier sheets 24 so as to occupy a generally rear half of the crotch region 28 and a generally front half of the rear waist region 29 of the chassis 21 except the rear end 31. The first panel 23 comprises a liquid-pervious sheet 40 (the liquid-pervious first sheet) facing the wearer, a liquid-impervious sheet 41 facing away from the wearer and a liquid-absorbent core 42 (liquid-absorbent first core) interposed between these liquid-pervious sheet 40 and liquid-impervious sheet 41 and joined to respective inner surfaces of these sheets 40, 41. The core 42 has its upper surface entirely covered with the liquid-pervious sheet 40 and its lower surface entirely covered with the liquid-impervious sheet 41.

The first panel 23 has a front portion 43 joined to the rear half of the crotch region 28 of the chassis 21 and a rear portion 44 joined to the front half of the rear waist region 29 of the chassis 21 and transversely side edges 45 joined to the respective side edges 32 of the chassis 21. Each of the front and rear portions 43, 44 are formed from the sheets 40, 41 and the core 42. The transversely opposite side edges 45 are formed from the sheets 40, 41 overlapped together. In these front and rear portions 43, 44 and the transversely side edges 45, the liquid-impervious sheet 41 is joined to the chassis 21 (the nonwoven fabric layer 25). In the first panel 23, longitudinally opposite ends 47 of the sheet 40 as well as longitudinally opposite ends 48 of the sheet 41 extend outward in the longitudinal direction beyond longitudinally opposite ends 46 of the core 42 and transversely opposite side edge portions 50 of the sheet 40 as well as transversely opposite side edge portions 51 of the sheet 41 extend outward in the transverse direction beyond transversely opposite side edges 49 of the core 42. The respective ends 47, 48 of the sheet 40, 41 are overlapped and joined together while the respective side edge portions 44, 45 of the sheets 40, 41 are overlapped and joined together.

The second panel 24 is shaped in a rectangular shape which is relatively long in the longitudinal direction and laid between the respective distal sections 63 of the leak-barrier sheets 22 so as to occupy a generally rear half of the front waist region 27 except the front end 30 and a generally front half of the crotch region 28 of the chassis 21. The second panel 24 comprises a liquid-pervious sheet 52 (liquid-pervious second sheet) facing the wearer, a liquid-pervious sheet 53 (liquid-pervious second sheet) facing away from the wearer and a liquid-absorbent core 54 (liquid-absorbent second core) interposed between the sheets 52, 53 and joined to the respective inner surfaces of these sheets 52, 53. The core 54 has its upper surface entirely covered with the liquid-pervious sheet 52 and its lower surface entirely covered with the liquid-pervious sheet 54.

The second panel 24 has a front portion 55 joined to the rear half of the front waist region 27 of the chassis 21, a distal portion 56 lying in the front half of the crotch region 28 of the chassis 21, and transversely opposite side edges 57 (transversely opposite side edge zones) joined to the respective lateral sections 32 of the chassis 21. The front portion 55 and the distal portion 56 are formed from the sheets 52, 53 and the core 54. The transversely opposite side edges 57 are formed from the sheets 52, 53 overlapped together. In the front portion 55 and the transversely opposite side edges 57, the liquid-pervious sheet 53 is joined to the chassis 21 (the nonwoven fabric layer 25). In the second panel 24, longitudinally opposite ends 59, 60 of the sheets 52, 53 extend outward in the longitudinal direction beyond longitudinally opposite ends 58 of the core 54 and transversely opposite side edges 62, 63 of the sheets 52, 53 extend outward in the transverse direction beyond transversely opposite side edges 61 of the core 54. In the second panel 24, the respective ends 59 of the sheets 52, 53 are overlapped and joined together while the respective side edges 62, 63 of the sheets 52, 53 are overlapped and joined together. In an inner end portion 64 of the distal portion 56, the respective ends 59, 60 of the sheets 52, 53 are folded toward the lower surface of the core 54.

The distal portion 56 of the second panel 24 comprises a pair of side sections 65 respectively laid on the respective lateral sections 32 of the chassis 21 and a transversely middle section 66 extending between the side sections 65. The side sections 65 and the transversely middle section 66 are formed from the sheets 52, 53 and the core 54. The side sections 65 extend upward from the chassis 21 so as to describe circular arcs which are convex upward above the chassis 21. The transversely middle section 66 describes a circular arc which is convex upward above the side sections 65. The side sections 65 are partially joined to the intermediate section 39 of the distal section 35 positioned aside toward the distal edge 38 of the leak-barrier sheet 22. Along the side sections 65, the liquid-pervious sheet 52 has its outer surface joined to the leak-barrier sheet 22 by means of adhesives 67. Alternatively, the side section 65 may be entirely connected with the intermediate section 39 of the distal section 35 or the distal section 35 of the respective leak-barrier sheet 22 including the distal edge 38 may be joined entirely connected with the side section 65.

The maximum height dimension N1 as measured from a lower end 68 of the distal section 35 of the leak-barrier sheet 22 to the transversely middle section 66 of the distal portion 56 is larger than the maximum height dimension N2 as measured from the lower end 68 to the distal edge 38 of the distal section 35 of the leak-barrier sheet 22. Part of the transversely middle section 66 of the distal portion 56 (a transversely middle area of the transversely middle section 66) extends upward above the distal edge 38 of the distal section 35 of the leak-barrier sheet 22 (See FIG. 4). The distal edge 38, in turn, extends upward above the side section 65 of the distal portion 56.

The distal portion 56 of the second panel 24 is held up above the chassis 21 as the distal sections 35 of the respective leak-barrier sheets 22 rise above the chassis 21. A pocket 69 opening from the crotch region 28 toward the rear waist region 29 is formed between the chassis 21 and the distal portion 56 of the second panel 24. More specifically, the pocket 69 extends over a generally front half of the crotch region 28. Below the distal portion 56 of the second panel 24, a front end 70 of the front portion 43 of the first panel 23 extends into the pocket 69.

In the front waist region 27 of the chassis 21, the longitudinally opposite ends 36 of the respective leak-barrier sheets 22 are joined to the inner surface of the sheet 21 (the nonwoven fabric layer 25) and the ends 59, 60 of the respective liquid-pervious sheets 52, 53 are interposed between the chassis 21 (the nonwoven fabric layer 25) and the leak-barrier sheets 22 and joined to the chassis 21, and the sheets 22. In the rear waist region 29 of the chassis 21, the longitudinally opposite ends 36 of the respective leak-barrier sheets 22 are joined to the inner surface of the chassis 21 (the nonwoven fabric layer 25) and the longitudinally opposite ends 47 of the liquid-pervious sheet 40 as well as the longitudinally opposite ends 48 of the liquid-impervious sheet 41 are interposed between the chassis 21 (the nonwoven fabric layer 25) and the leak-barrier sheets 22 and joined to the chassis 21, and the sheets 22. Along the lateral sections 32 of the chassis 21, the proximal lateral sections 34 of the respective leak-barrier sheets 22 are joined to the inner surface of the chassis 21 and the side edge portions 50, 51, 62, 63 of the liquid-pervious sheets 40, 52, 53 and the liquid-impervious sheet 41 are interposed between the chassis 21 (the nonwoven fabric layer 25) and the leak-barrier sheets 22 and joined to the chassis 21 and the sheets 22.

The lateral sections 32 of the rear waist region 29 are respectively provided with a pair of flexible tape fasteners 71 comprising a fibrous nonwoven fabric. Each of these tape fasteners 71 has a proximal end portion 72 and a distal end portion 73 both extending in the transverse direction. The proximal end portion 72 is interposed between the nonwoven fabric layers 25, 26 and joined to mutually opposed surfaces of these nonwoven fabric layers 25, 26. The distal end portion 73 is provided on its inner surface with a hook member 74. The distal end portion 73 is folded inward as viewed in the transverse direction and temporarily anchored on the chassis 21 (the nonwoven fabric layer 25) by means of the hook member 74. It is possible without departing from the scope of the invention to replace the hook member 74 by pressure-sensitive adhesive applied on the distal end portion 73.

The front waist region 27 is provided with a flexible target tape strip 75 on which the distal end portion 73 of the tape fastener 71 is to be detachably anchored. The target tape strip 75 is shaped in a rectangle shape which is relatively long in the transverse direction and comprises a plastic film and a loop member (not shown) provided on this plastic film. More specifically, the plastic film is joined to the outer surface (the nonwoven fabric 26) of the chassis 21. When it is desired to coat the distal end portion 73 of the tape fastener 70 with a pressure-sensitive adhesive, a plastic film may be used as material for the target tape strip 75.

To put the article 20A on the wearer's body, the lateral sections 32 of the rear waist region 29 are placed upon the respective outer sides of the lateral sections 32 of the front waist region 27 and then the distal end portions 73 of the respective tape fasteners 71 are anchored on the target tape strip 75 by means of the respective hook members 74 to connect the front and rear waist regions 27, 29 with each other. Upon connection of the front and rear waist regions 27, 29 in this manner, the article 20A is formed with a waist-hole and a pair of leg-holes (not shown). Urine discharged onto the front waist region 27 and the front half of the crotch region 28 of the article 20A put on the wearer is absorbed and contained by the core 54 of the second panel 24 while feces moving toward the front waist region 27 are received by the pocket 69.

The distal portion 56 of the second panel 24 describes a circular arc which is convex upward above the chassis 21 and the pocket 69 opening from the crotch region 28 toward the rear waist region 29 is formed between the chassis 21 and the distal portion 56. In this way, the pocket 54 reliably receives feces if feces discharged onto the rear half of the crotch region 28 and the rear waist region 29 moves toward the front waist region 27. In the article 20A, urine is absorbed and contained by the second panel 24 while feces is absorbed and contained by the first panel 23 and then received by the pocket 69. In this way, urine and feces are separated from each other and thus the wearer's skin is reliably protected from being contaminated with mixture of urine and feces.

The side sections 65 of the distal portion 56 of the second panel 24 are joined to the distal sections 35 of the respective leak-barrier sheets 22 and thereby the distal portion 56 is held up above the chassis 21 by the distal sections 35 so that the distal portion 56 may be kept by the distal sections 35 in an upward convex shape and the side sections 65 extending upward above the chassis 21 may be protected being unintentionally collapsed. Thus the pocket 69 is hardly closed and reliably receives feces.

The transversely middle section 66 of the distal portion 56 extends above the distal edges 38 of the distal sections 35 of the leak-barrier sheets 22 so that the transversely middle section 66 is in close contact with an intermediate region defined between the genital organ and the anus of the wearer and thereby forms the barrier adapted to divide the genital organ and the anus off from each other. In this way, urine and feces can be reliably separated from each other and thereby the wearer's skin can be reliably protected from contaminated with mixture of urine and feces.

The distal edge 38 of the distal sections 35 of the respective leak-barrier sheets 22 extend above the side sections 65 of the distal portion 56 in the second panel 24. These distal edges 38 stand in the way of urine spreading on the upper surface of the second panel 24 (the upper surface of the liquid-pervious sheet 52) and prevent urine from leaking sideways beyond the transversely opposite side edges 57 even if such urine moves toward the side edge zones 57. The transversely middle section 66 of the distal portion 56 lies at level above the distal edges 38 comes in contact with the wearer's skin ahead of the distal edges 38. Therefore, it is unlikely that the distal edges 38 might be collapsed in the transverse direction of the article 20A and the function of these distal edges 38 as the barriers against urine might be disabled. Barriers formed from the distal sections 35 of the respective leak-barrier sheets 22 against urine are effective to prevent urine from leaking sideways beyond the lateral sections 32 of the chassis 21 even if urine spreading on the upper surface of the first panel 23 (the upper surface of the liquid-pervious sheet 40) flows toward the lateral sections 32.

The front end 70 of the first panel 23 underlies the distal portion 56 of the second panel 24 and extends into the pocket 69. Such an arrangement allows urine as well as feces to be absorbed and contained by the core 42 of the firs 69 and thereby prevents urine and feces from being mixed with each other even if urine permeate the second panel 24 into the pocket 69. Furthermore, it is unlikely that the first and second panels 23, 24 might overlap each other in the front and rear waist region 27, 29 to make these panels 23, 24 and the wearer of the article 20A might suffer from a feeling of discomfort.

Figure 5:
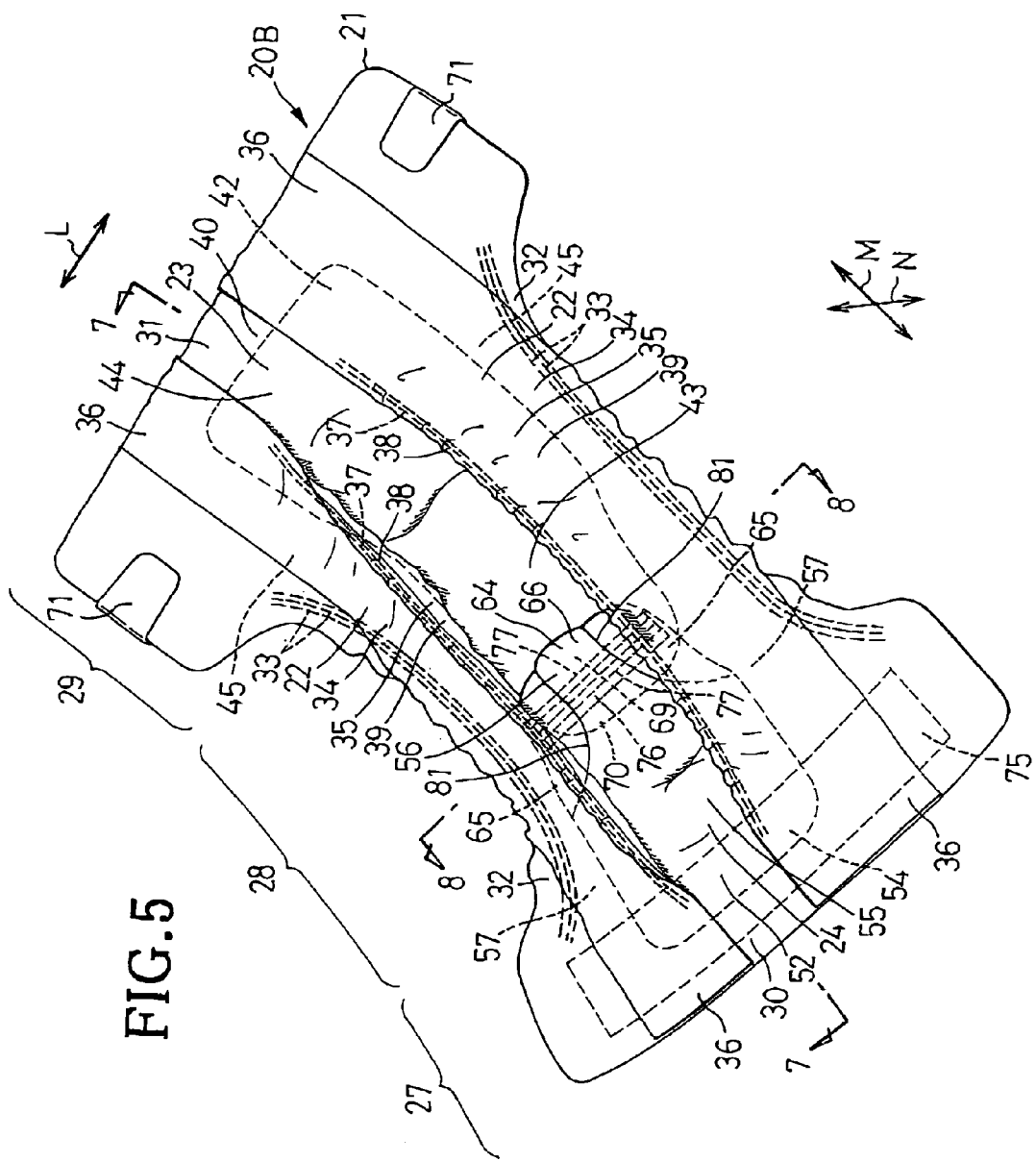
FIG. 5 is a perspective view showing a disposable wearing article according to another embodiment of the invention.
Figure 6:
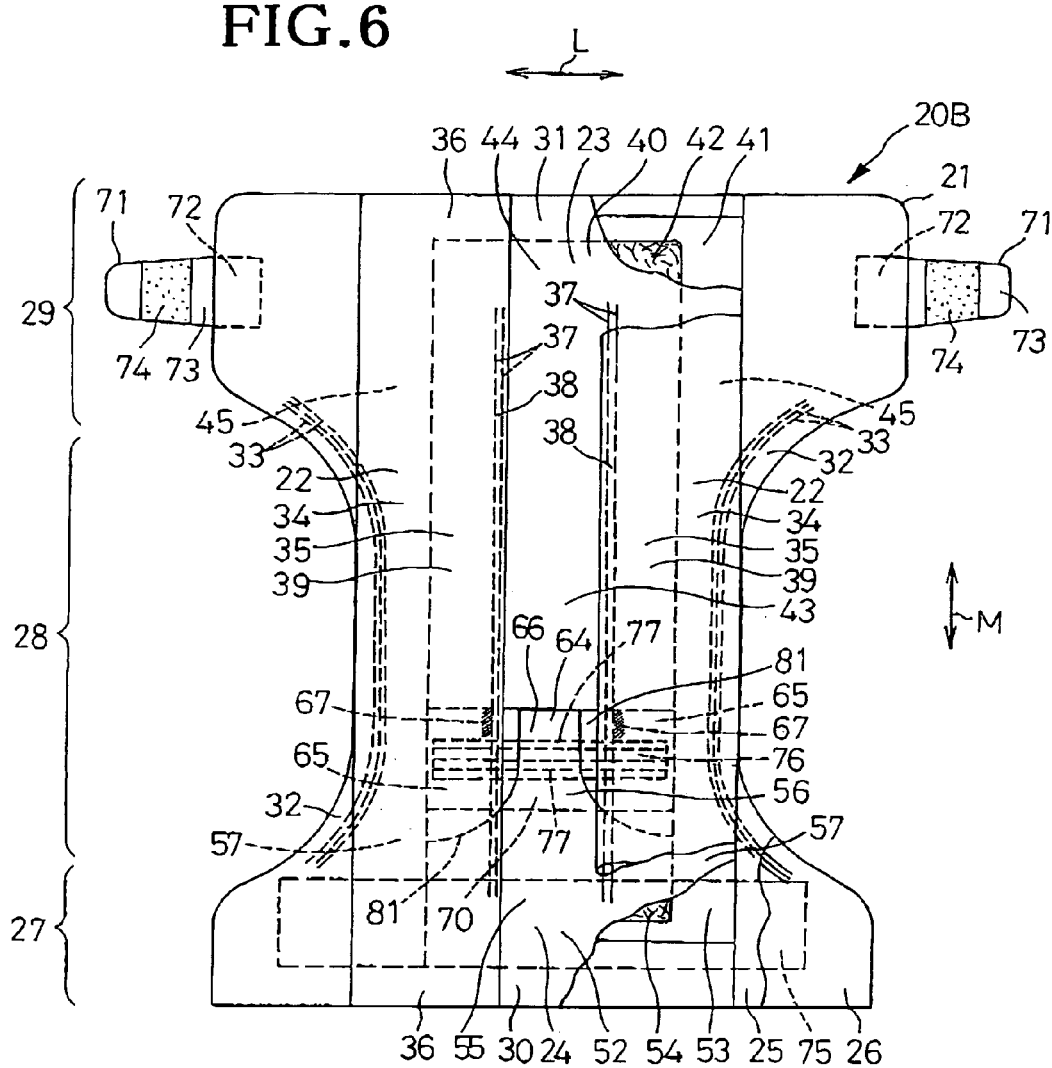
FIG. 6 is a partially cutaway plan view showing the wearing article of FIG. 5 as viewed from the side of the panel.
Figure 7:
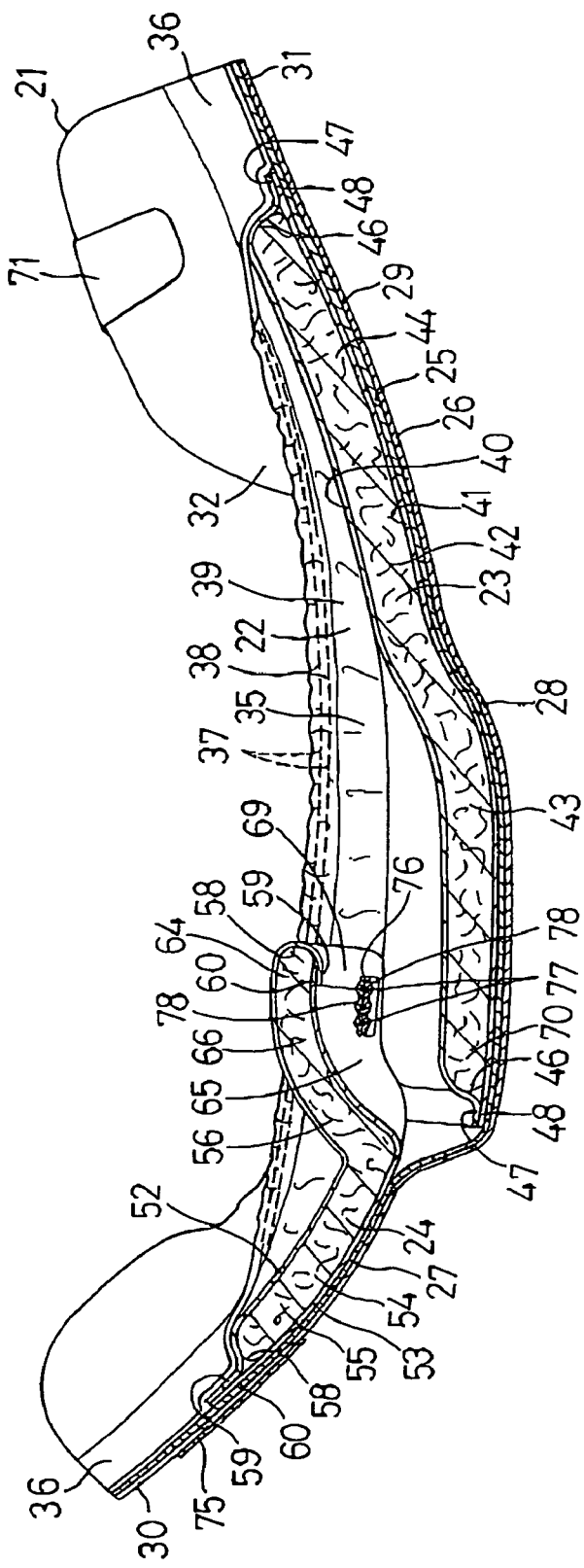
FIG. 7 is a sectional view taken along the line 7—7 in FIG. 5.
Figure 8:
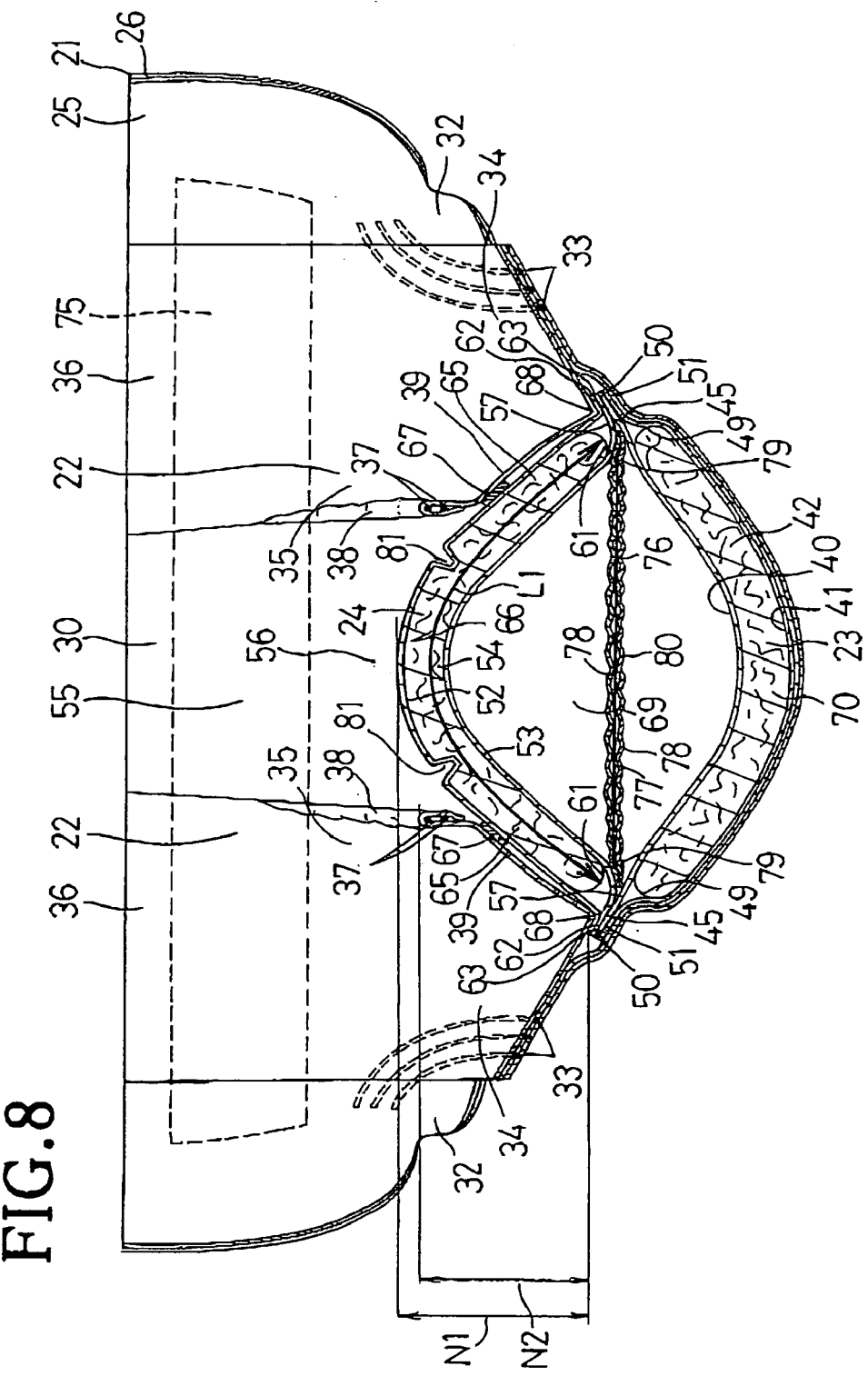
FIG. 8 is a sectional view taken along the line 8—8 in FIG. 5.

FIG. 5 is a perspective view showing a disposable wearing article 20B according to another embodiment of the invention, FIG. 6 is a partially cutaway plan view showing the article 20B of FIG. 5 as viewed from the side of first and second panels 23, 24, FIG. 7 is a sectional view taken along a line 7—7 in FIG. 5 and FIG. 8 is a sectional view taken along a line 8—8 in FIG. 5. In FIGS. 5 and 6, a transverse direction is indicated by an arrow L, a longitudinal direction is indicated by an arrow M and a thickness direction is indicated by an arrow N (in FIG. 5 alone). FIG. 6 shows the article 20B as developed against contractile force of elastic members 33, 37, 77 in the longitudinal direction as well as in the transverse direction.

This article 20B is similar to the article 20A of FIG. 1–4 except an arrangement such that the pocket 69 is provided with a spacer 76 extending in the transverse direction and the second panel 24 is formed with folding guides 81. The components similar to those in the article 20A of FIG. 1–4 are designated by the same reference numerals as those in FIG. 1–4 and the similar arrangements as those of the article 20A of FIG. 1–4 will not be repetitively described here.

The spacer 76 is elastically stretchable in the transverse direction and contractibly attached to the pocket 69. Specifically, the spacer 76 comprises a water-pervious sheet 78 to which a plurality of elastic members 77 extending in the transverse direction are contractibly attached. These elastic members 77 are secured to the sheet 75 while the elastic members 77 are stretched at a predetermined ratio in the transverse direction. The spacer 76 has transversely opposite fixed ends 79 joined to the respective side sections 65 of the distal portion 56 and an intermediate portion 80 extending between these ends 79. The side sections 65 of the distal portion 56 are drawn inward as viewed in the transverse direction of the chassis 21 under contractile force of the spacer 76. The transversely opposite side edges 45 of the first panel 23 are drawn inward as viewed in the transverse direction under the contractile force of the spacer 76 and the front portion 43 is bent so as to describe a circular arc which is convex to a downward direction together with the chassis 21.

Alternatively, the transversely opposite fixed ends 79 of the spacer 76 may be joined to at least one of the side sections 65 and the side edges 57 of the distal portion 56. The fixed ends 79 may be interposed between the transversely opposite side edges 45 of the first panel 23 and the transversely opposite side edges 57 of the second panel 24 and joined to these side edges 45, 57. It is possible to adopt the spacer 76 made of an elastically stretchable water-pervious sheet having none of the elastic members, for example, an elastically stretchable hydrophilic fibrous nonwoven fabric. It is also possible to adopt the spacer 76 made of a non-stretchable water-pervious sheet alone, for example, a hydrophilic fibrous nonwoven fabric. When it is desired to adopt the spacer 76 made of such a non-stretchable water-pervious sheet, the spacer 76 is exploited to have a transverse dimension smaller than a transverse dimension between the transversely opposite side edges 61 of the core 54 constituting the second panel 24 so that the leg-like potions 65 of the distal portion 56 may be drawn inward as viewed in the transverse direction of the chassis 21.

The distal portion 56 of the second panel 24 is formed with a pair of folding guides 81 extending in a generally longitudinal direction and spaced apart from each other by a predetermined dimension in the transverse direction between the respective side section 65 and the transversely middle section 66. Specifically, these folding guides 81 extend to the transversely opposite side edges 57 on the side of the front portion 55, describing circular arcs which are convex inward as viewed in the transverse direction of the chassis 21 so that a distance between the folding guides 81 gradually increases from the distal edge 64 of the distal portion 56 toward the front portion 55. The distal portion 56 of the second panel 24 is folded along the folding guides 81.

The core 54 along the folding guides 81 have a density and a basis weight less than those of the core 54 except for the folding guides 81. Correspondingly, the second panel 24 along these folding guides 81 present a stiffness lower than that presented by the second panel 24 except for the folding guides 81. Alternatively, the folding guides 81 may not contain the core 54, i.e., the folding guides 81 may be formed from the liquid-pervious sheets 52, 53 except for the core 54. An alternative arrangement is also possible such that on the distal portion 56 the folding guides 81 extend from the distal edge 64 and terminate short of the transversely opposite fixed side edges 57.

The side sections 65 are partially joined to the intermediate sections 39 of the distal section 35 positioned aside toward the distal edges 38 of the respective leak-barrier sheets 22 in the vicinity of the folding guides 81.

The distal portion 56 of the second panel 24 is folded along the respective folding guides 81 with the side sections 65 thereof drawn inward as viewed in the transverse direction of the chassis 21 under the contractile force of the spacer 76 and held up above the chassis 21 by the distal sections 35 of the respective leak-barrier sheets 22.

The front portion 43 of the first panel 23 is bent so as to describe a circular arc which is convex to a downward direction together with the chassis 21 so that, compared to the article 20A of FIG. 1, the article 20B can receive a larger amount of feces.

The spacer 76 which is elastically stretchable in the transverse direction is contractibly attached to the pocket 69 so that the side sections 65 of the distal portion 56 may be drawn inward as viewed in the transverse direction of the chassis 21. Such arrangement ensures that the distal portion 56 is kept by the distal sections 35 in the upward convex shape without the anxiety that the side sections 65 extending upward above the sheet 21 might be unintentionally collapsed to close the opening of the pocket 69. Even when the wearer's body pressure is exerted upon the article 20B in its thickness direction and the front portion 43 of the first panel 23 as well as the distal portion 56 of the second panel 24 are collapsed, just at the moment that the article 20B is relieved of the body pressure, contractile force of the spacer 76 causes the front portion 43 to be depressed so as to describe a circular arc which is convex to a downward direction d and causes the distal portion 56 to rise above the chassis 21 so as to describe a circular arc which is convex to a upward direction. Consequently, the pocket 69 is formed again between the chassis 21 and the distal portion 56.

The side sections 65 constituting the distal portion 56 of the second panel 24 are joined to the distal sections 35 of the respective leak-barrier sheets 22 in the vicinity of the respective folding guides 81 so that the distal portion 56 are folded along the folding guides 81 as the respective distal sections 35 raise the distal portion 56 above the chassis 21. In this way, the distal portion 56 is reliably folded along the respective folding guides 81. The distal portion 56 of the second panel 24 are folded along the folding guides 81 and thereby the distal portion 56 is clearly defined into the side sections 65 lying outside the respective folding guides 81 and the transversely middle section 66 extending between the folding guides 81. Such feature facilitates the side sections 65 to rise above the chassis 21 and at the same time facilitates the distal portion 56 to become convex upward above the chassis 21. Thus the pocket 69 is reliably formed between the chassis 21 and the distal portion 56.

A transverse dimension of the spacer 76 in its contracted state is preferably in a range of 20 to 93%, more preferably in a range of 50 to 80% with respect to a transverse dimension L1 between the transversely opposite side edges 61 of the core 54 constituting the second panel 23.

The spacer 76 including the elastic member 77 has a tensile stress in the transverse direction in a range of 0.5 to 1.5 N at 100 to 250% stretched state. If the tensile stress of the spacer 76 is less than 0.5 N, the side sections 65 of the free rear portion 56 will be insufficiently drawn inward as viewed in the transverse direction of the chassis 21 under contractile force of the spacer 76 and, even if a slight body pressure is exerted upon the article 20B, the distal portion 56 may be readily collapsed to close the opening of the pocket 69. If the tensile stress of the spacer 76 exceeds 1.5 N, the crotch region 28 will be excessively contracted inward in the transverse direction under the contractile force of the spacer 76, resulting in formation of a plurality of irregular gathers in the chassis 21, the front portion 43 of the first panel 23 and the distal portion 56 of the second panel 24. These irregular gathers will make it difficult not only to maintain the desired shape of the pocket 69 and, in addition, deteriorate the desired body fluid absorbing function of the first and second panels 23, 24. Consequentially, adequate absorption of urine and feces will be impossible in the crotch region 28. The article 20B with the spacer 76 having the tensile stress in the range as specified above allows the pocket 69 formed between the chassis 21 and the distal portion 56 of the second panel 24 to be reliably kept in the desired shape without deteriorating the body fluid absorbent function of the first and second panels 23, 24 in the crotch region 28. The tensile stress of the spacer 76 was measured by the method as follows:

(1) The spacer 76 (inclusive of the elastic members 77) was separated from the article 20B and the spacer 76 and then the spacer 73 was cut to obtain samples for measurement of the stretch stress having a longitudinal dimension of 30 mm and a transverse dimension of 100 mm. For measurement of the stretch stress of the spacer 76, the Tensile Tester manufactured by SHIMADZU CORPORATION in Japan was used.

(2) Transversely opposite side edge portions of the sample contracted under a contractile force of the elastic members 77 were clamped by respective chucks of the Tensile Tester (a dimension over which each end portion was clamped by the chuck: about 30 mm, a length dimension of the sample measured between the chucks: about 100 mm). The sample was stretched in the transverse direction at a rate of 100 mm/min and, after the sample had been stretched by 260%, the tension was relieved. The sample was stretched again in the transverse direction at a rate of 100 mm/min and a force exerted on the Tester at the moment the sample was stretched by 100 to 250% was measured as the tensile stress of the spacer in the transverse direction. The tensile stress in the transverse direction of the sample having been measured in this manner was in a range of 0.5 to 1.5 N. As used herein "the sample was stretched by 200%" means that, for example, the sample having its transverse dimension of 30 mm was stretched to 30 mm×2.0=60 mm.

The distal portion 56 (containing the core 54) of the second panel 24 including the folding guides 81 has a transverse flexural stiffness in a range of 0.5 to 1.5 mN and the distal portion 56 (containing the core 54) of the second panel 24 except for the folding guides 81 has a transverse flexural stiffness in a rang of 1.0 to 2.0 mN. If the stiffness of the distal portion 56 (containing the core 54) including the folding guides 81 exceeds 1.5 mN, it will be difficult to tuck the distal portion 56 along the folding guides 81 and to raise the side sections 65 above the chassis 21. If the stiffness of the distal portion 56 in except for the folding guides 81 is less than 1.0 mN, the distal portion 56 will be excessively contracted inward as viewed in the transverse direction of the chassis 21 under a contractile force of the spacer 76 and it will be impossible to keep the pocket 69 in its effective shape. If the stiffness of the distal portion 56 of the second panel 24 except for the folding guides 81 extends exceeds 2.0 mN, a flexibility of the second panel 24 will be deteriorated and the second panel 24 coming in contact with the article wearer's skin may uncomfortably irritate the article wearer. These stiffness values were measured using the Gurley Method (JIS L 1096-01-8.20.1) as follows:

(1) The second panel 24 was taken off from the article 20B and the second panel 24 was cut to obtain samples each having a longitudinal dimension of 25 mm and a transverse dimension of 30 mm for measurement of stiffness values. As the samples for this measurement, the first sample (containing the core 54) including the folding guides 81 and the second sample (containing the core 54)

except for the folding guides 81 were prepared. For measurement of the flexural stiffness, the Gurley's Stiffness Tester was used.

(2) One of longitudinally opposite end portions of the first sample was held by a chuck of the tester and the other end portion was maintained in engagement with a pendulum of the tester and the tester was initialized by loading an auxiliary weight so that the tester scale may point the readings in a range of 3 to 6; the tester was turned on and a scale reading of the moment at which the pivot rod of the pendulum was separated from the first sample was recorded as a first stiffness value. Now the other of longitudinally opposite ends of the first sample was held by the chuck of the tester and one of these end was maintained in engagement with the pendulum of the tester. The tester was initialized by loading the auxiliary weight so that the tester scale may point the readings in a range of 3 to 6; the tester was turned on and the scale reading of the moment at which the pivot rod of the pendulum was separated from the sample was recorded as a second stiffness value. An average value of these first and second stiffness values obtained in this manner was recorded as the stiffness value of the first sample and the flexural stiffness value of the first sample was recorded as the flexural stiffness value of the distal portion 56 including the folding guides 81. The flexural stiffness value of the first sample was in a range of 0.5 to 1.5 mN.

(3) One of longitudinally opposite ends of the second sample was held by the chuck of the tester and the other end portion was maintained in engagement with the pendulum of the tester and the tester was initialized by loading an auxiliary weight so that the tester scale may point the reading in a range of 3 to 6; the tester was turned on and a scale reading of the moment at which the pivot rod of the pendulum was separated from the second sample was recorded as a third stiffness value. Now the other of longitudinally opposite ends of the second sample was held by the chuck of the tester and the one of these ends was maintained in engagement with the pendulum of the tester. The tester was initialized by loading the auxiliary weight so that the tester scale may point the scale reading in a range of 3 to 6; the tester was turned on and the scale reading of the moment at which the pivot rod of the pendulum was separated from the sample was recorded as a fourth stiffness value. An average value of these third and fourth stiffness values obtained in this manner was recorded as the stiffness value of the distal portion 56 except for the folding guides 81. The flexural stiffness value of the second sample was in a range of 1.0 to 2.0 mN.

Figure 9:
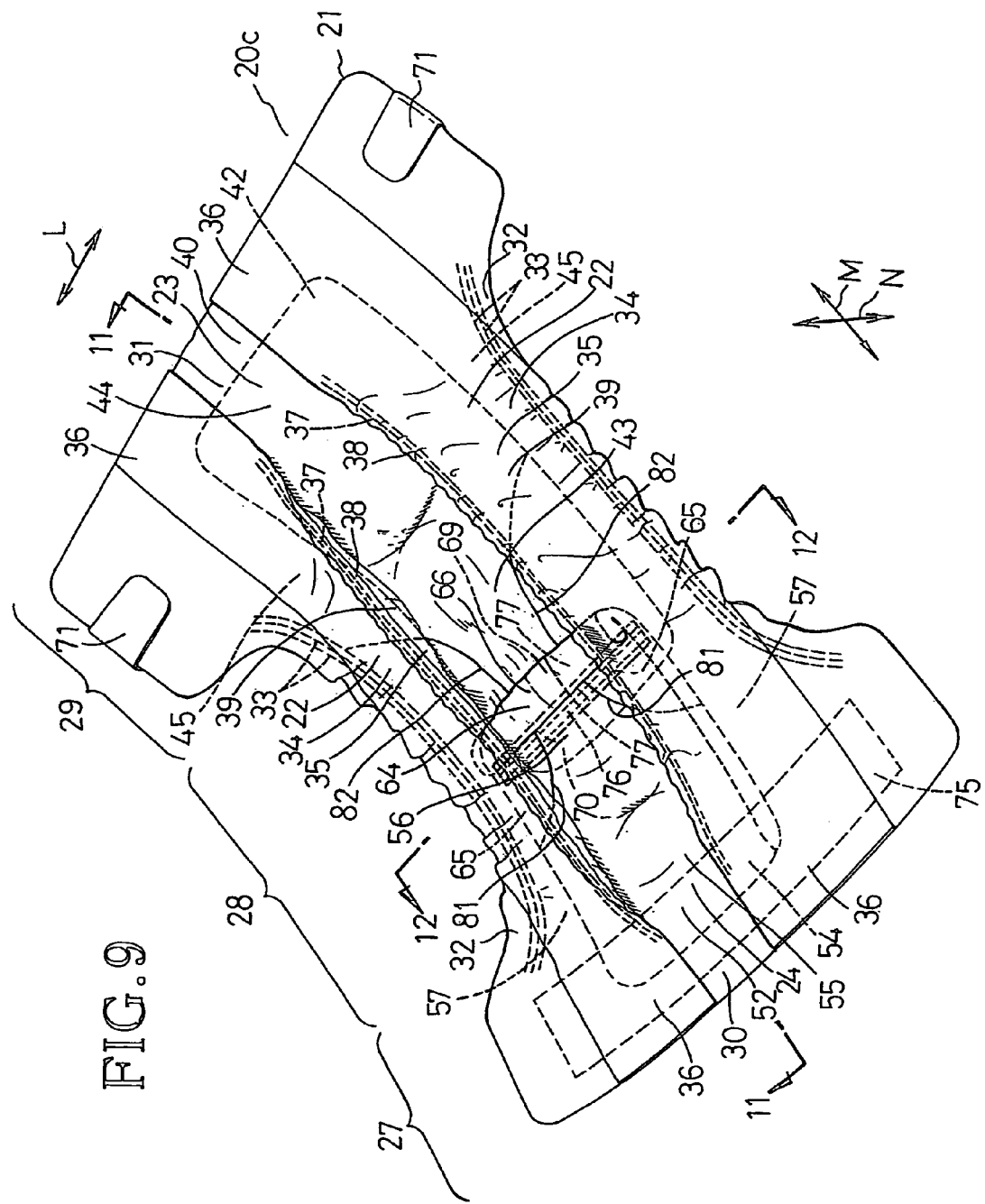
FIG. 9 is a perspective view showing a disposable wearing article according to still another embodiment of the invention.
Figure 10:
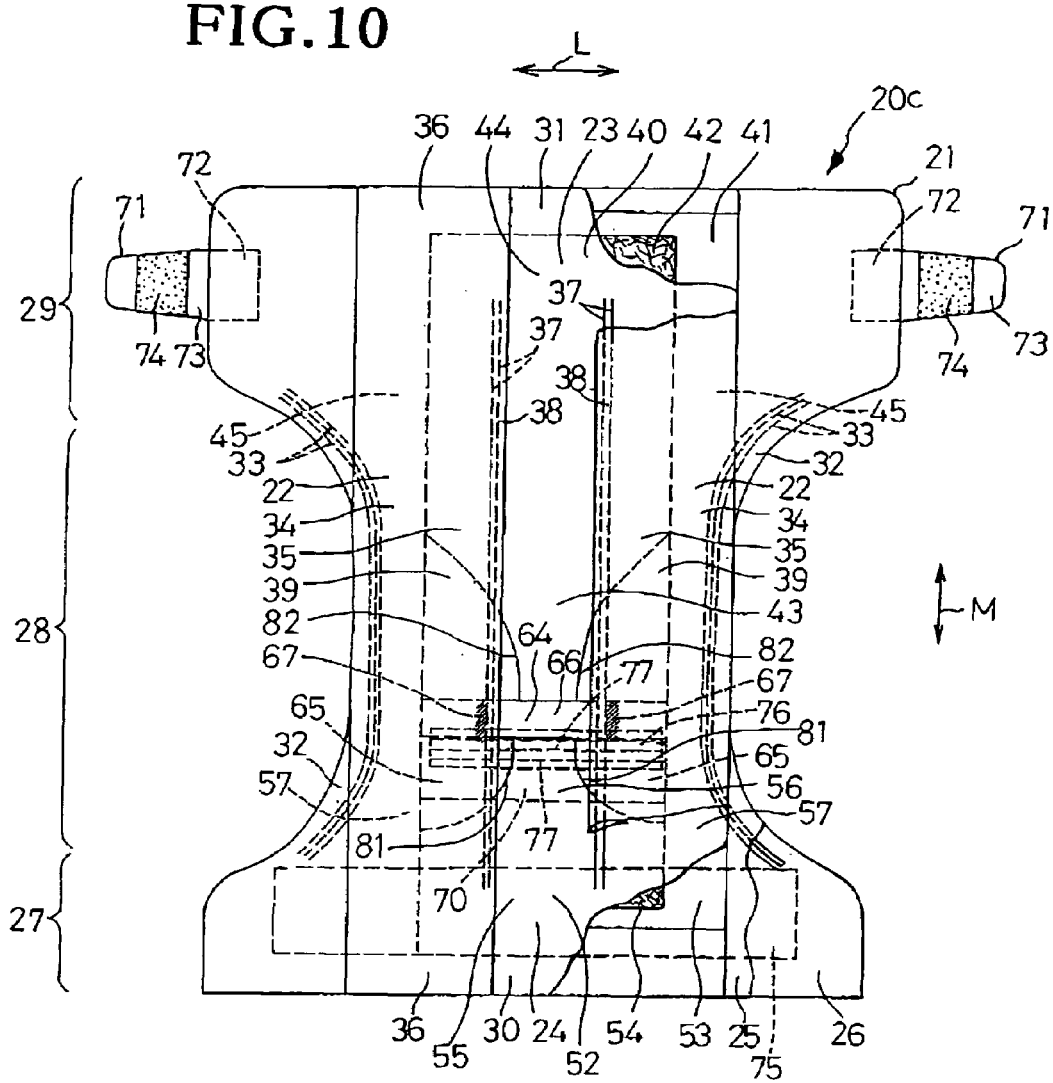
FIG. 10 is a partially cutaway plan view showing the article of FIG. 9 as viewed from the side of the panel.
Figure 11:
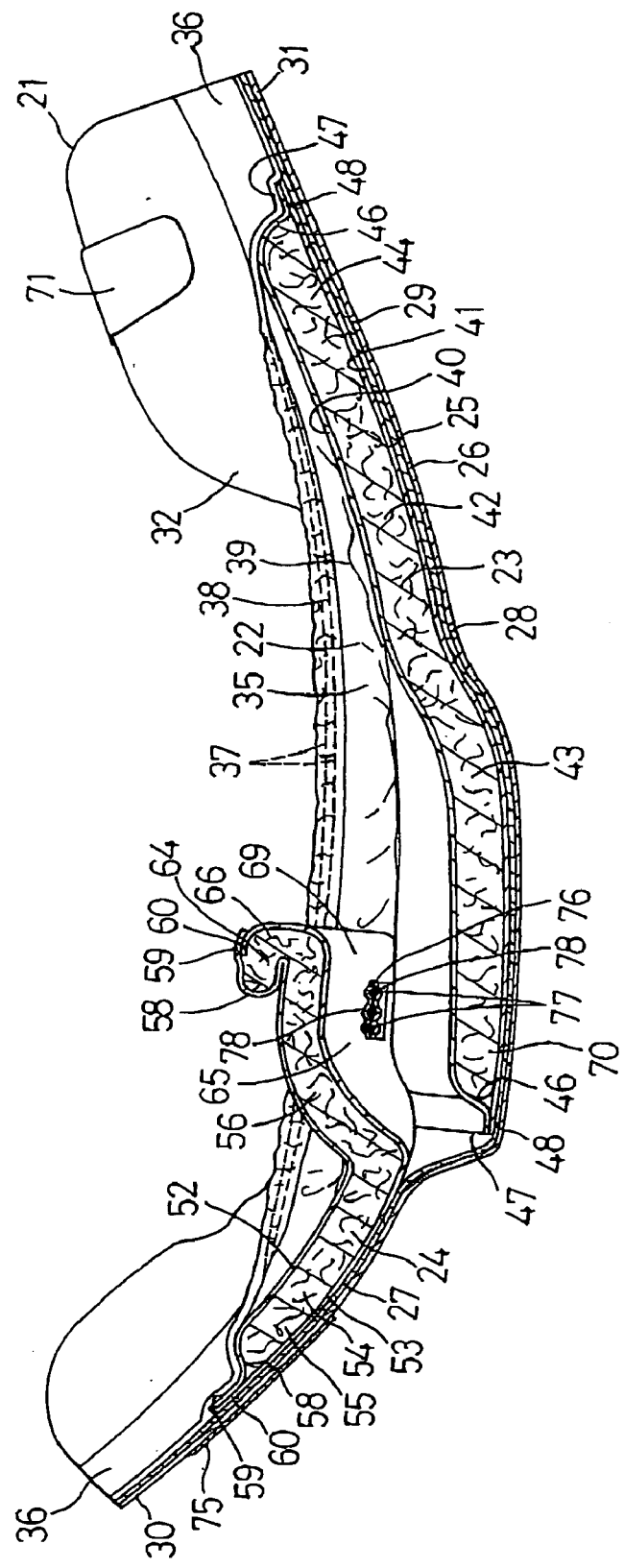
FIG. 11 is a sectional view taken along the line 11—11 in FIG. 9.
Figure 12:
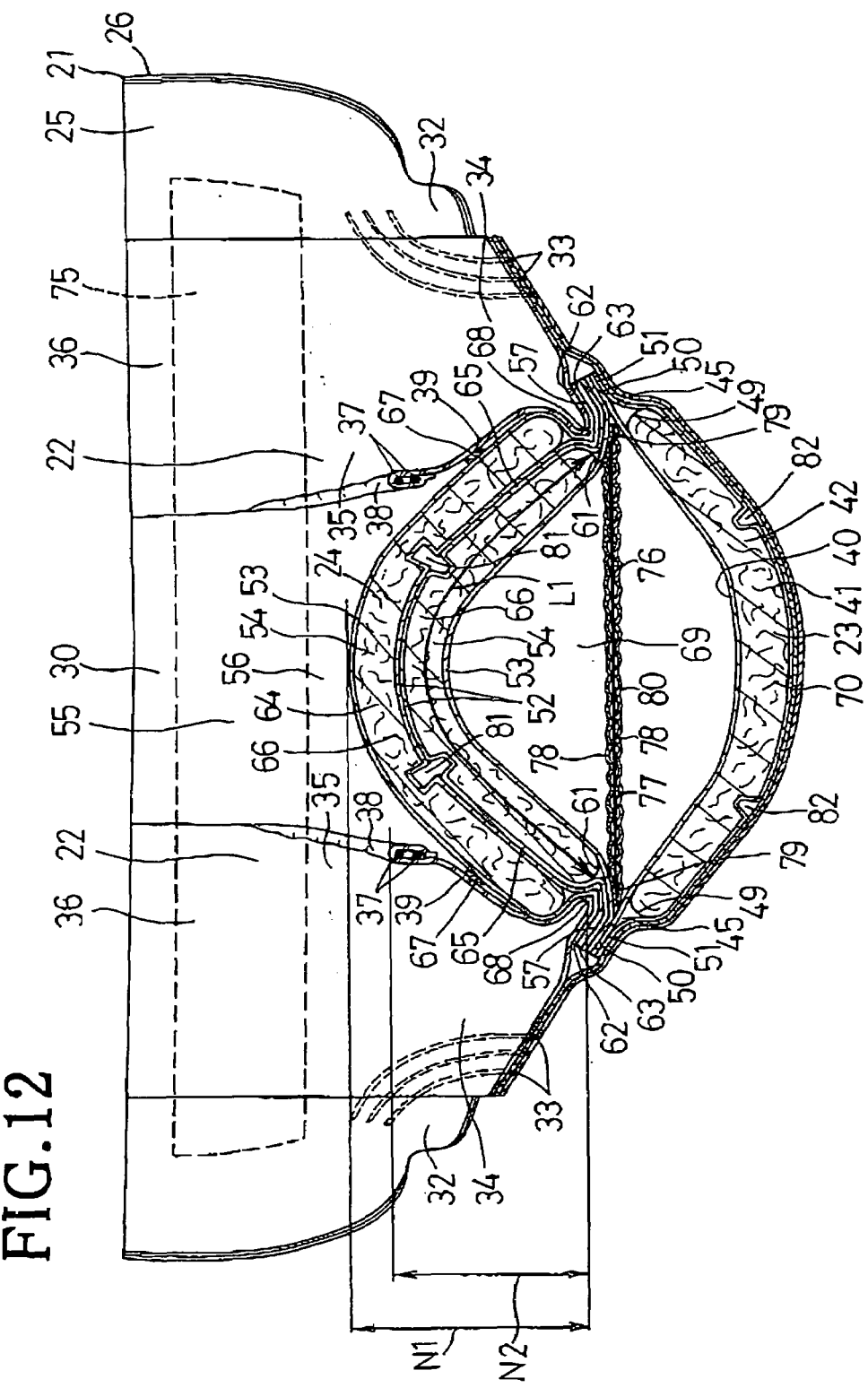
FIG. 12 is a sectional view taken along the line 12—12 in FIG. 9.

FIG. 9 is a perspective view showing a disposable wearing article 20C as still another embodiment of the invention, FIG. 10 is a partially cutaway plan view showing the article 20C of FIG. 9 as viewed from the side of first and second panels 23, 24, FIG. 11 is a sectional view taken along a line 11—11 in FIG. 9 and FIG. 12 is a sectional view taken along a line 12—12 in FIG. 9. In FIGS. 9 and 10, a transverse direction is indicated by an arrow L, a longitudinal direction is indicated by an arrow M and a thickness direction is indicated by an arrow N (in FIG. 9 alone). FIG. 10 shows the article 20C as developed against contractile force of elastic members 33, 37, 77 in the longitudinal direction as well as in the transverse direction.

This article 20C is similar to the article 20B of FIG. 5–8 except an arrangement such that the first panel 23 is further formed with folding guides 82 and the distal edge 64 of the distal portion 56 is folded upward onto the second panel 24.

The components similar to those in the article 20B of FIG. 5–8 are designated by the same reference numerals as those in FIG. 5–8 and the similar arrangements as those of the article 20B of FIG. 5–8 will not be repetitively described here.

The front portion 43 of the first panel 23 is formed with a pair of folding guides 82 extending in a generally longitudinal direction and spaced apart from each other by a predetermined dimension in the transverse direction. Specifically, these folding guides 82 extend to the transversely side edges 45 on the side of the rear portion 44, describing circular arcs which are convex inward as viewed in the transverse direction of the chassis 21 gradually increases from the front end 70 of the front portion 43 toward the rear portion 44. The transversely opposite side edges 45 are drawn inward as viewed in the transverse direction of the chassis 21 under the contractile force of the spacer 76. In response to this, the front portion 43 is folded along the respective folding guides 82 so that the front portion 43 is bent so as to describe a circular arc which is convex to a downward direction together with the chassis 21 in the thickness direction of the article 20C.

The core 42 along the folding guides 82 have a density and a basis weight less than those of the core 42 except for the folding guides 82. Correspondingly, the first panel 23 along these folding guides 82 present a stiffness lower than that presented by the first panel 24 except for the folding guides 82.

Alternatively, the folding guides 82 may not contain the core 42, i.e., the folding guides 82 may be formed from the liquid-pervious sheets 40, 41 except for the core 42. An alternative arrangement is also possible such the folding guides 82 extend from terminate short of the transversely opposite fixed side edges 45.

The distal edge 64 of the distal portion 56 is folded upward onto the second panel 24. The side sections 65 are partially joined to the intermediate sections 39 of the distal section 35 positioned aside toward the distal edges 38 of the respective leak-barrier sheets 22 in the vicinity of the folding guides 81.

The maximum height dimension N1 as measured from the lower end 68 of the distal section 35 of the leak-barrier sheet 22 to the transversely middle section 66 of the distal portion 56 is larger than the maximum height dimension N2 as measured from the lower end 68 to the distal edge 38 of the distal section 35 of the leak-barrier sheet 22. The transversely middle section 66 folded upward extends upward above the end portion 38 of the distal section 35 of the leak-barrier sheet 22. The distal edge 38, in turn, extends upward above the side section 65.

The front end 70 of the first panel 23 underlies the distal portion 56 of the second panel 24 and extends into the pocket 69. The front end 70 is bent so as to describe a circular arc which is convex to a downward direction together with the chassis 21 and thereby forms the pocket 69.

The front portion 43 of the first panel 23 is bent so as to describe a circular arc which is convex to a downward direction together with the chassis 21 so that, compared to the article 20A of FIG. 1, the article 20C can receive a larger amount of feces.

The distal edge 64 of the distal portion 56 is folded upward onto the second panel 24 and extends upward beyond the distal edge 38 of the distal sections 35 of the respective leak-barrier sheets 22 so that the transversely middle section 66 of the distal edge 64 folded in this manner reliably comes in close contact with the intermediate region defined between the genital organ and the anus of the wearer as the article 20C is put on the wearer's body and thereby forms the barrier adapted to divide the genital organ and the anus off from each other.

Figure 13:
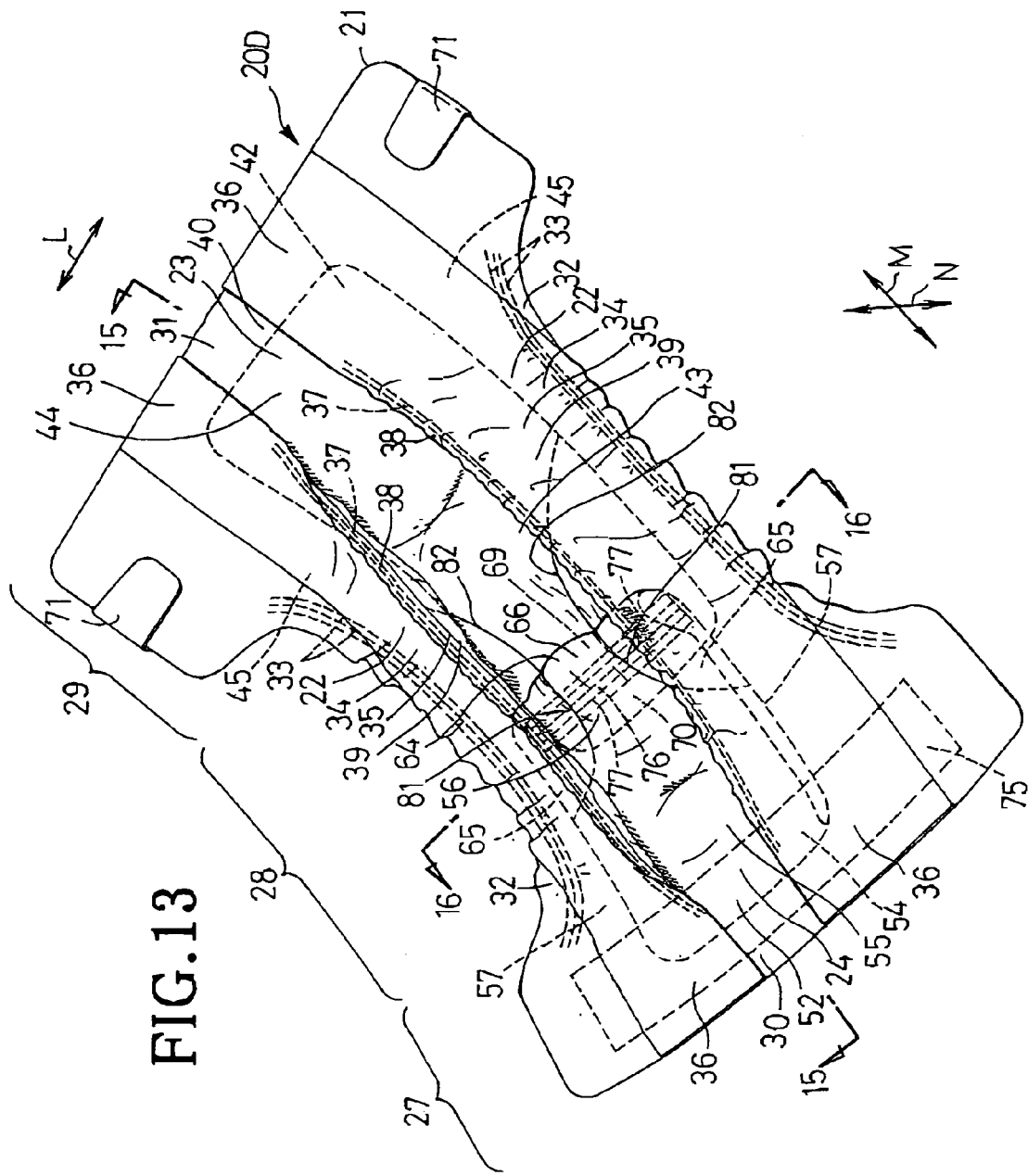
FIG. 13 is a perspective view showing a disposable wearing article according to further another embodiment of the invention.
Figure 14:
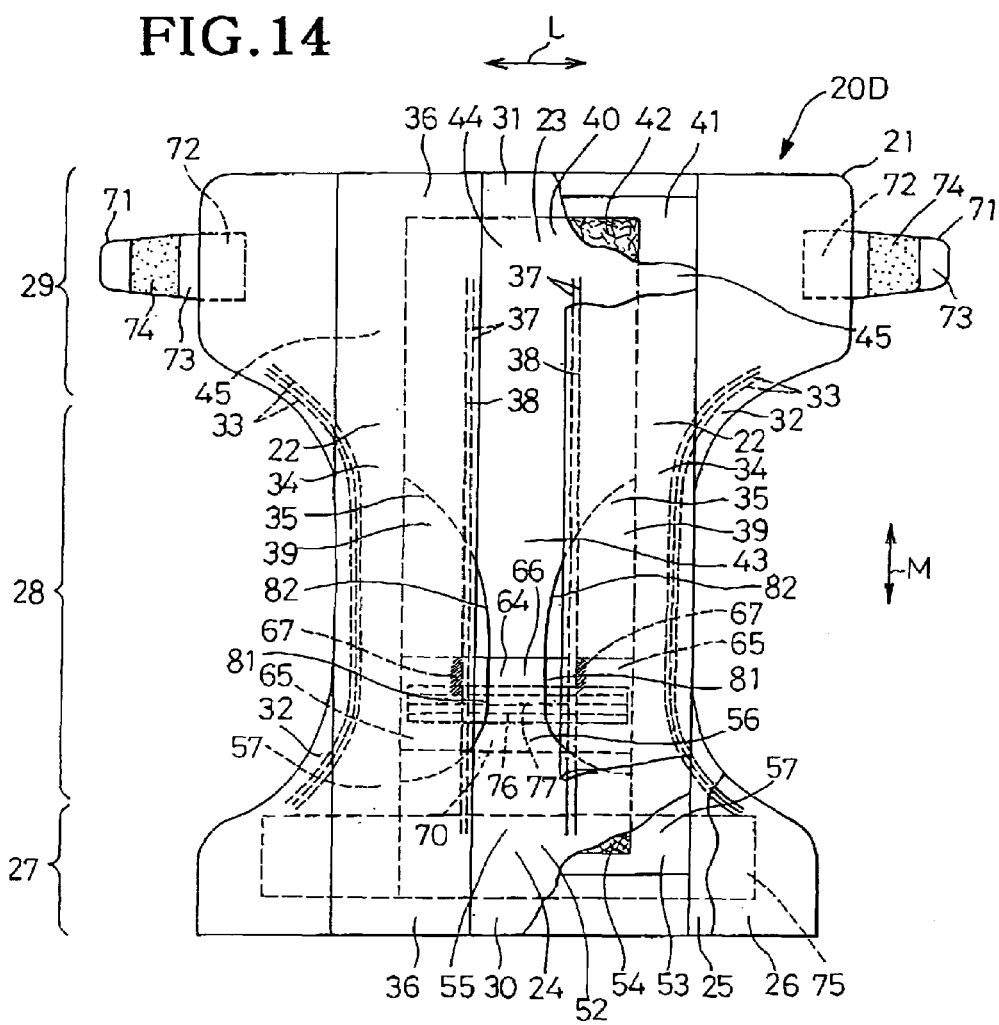
FIG. 14 is a partially cutaway plan view showing the article of FIG. 13 as viewed from the side of the panel.
Figure 15:
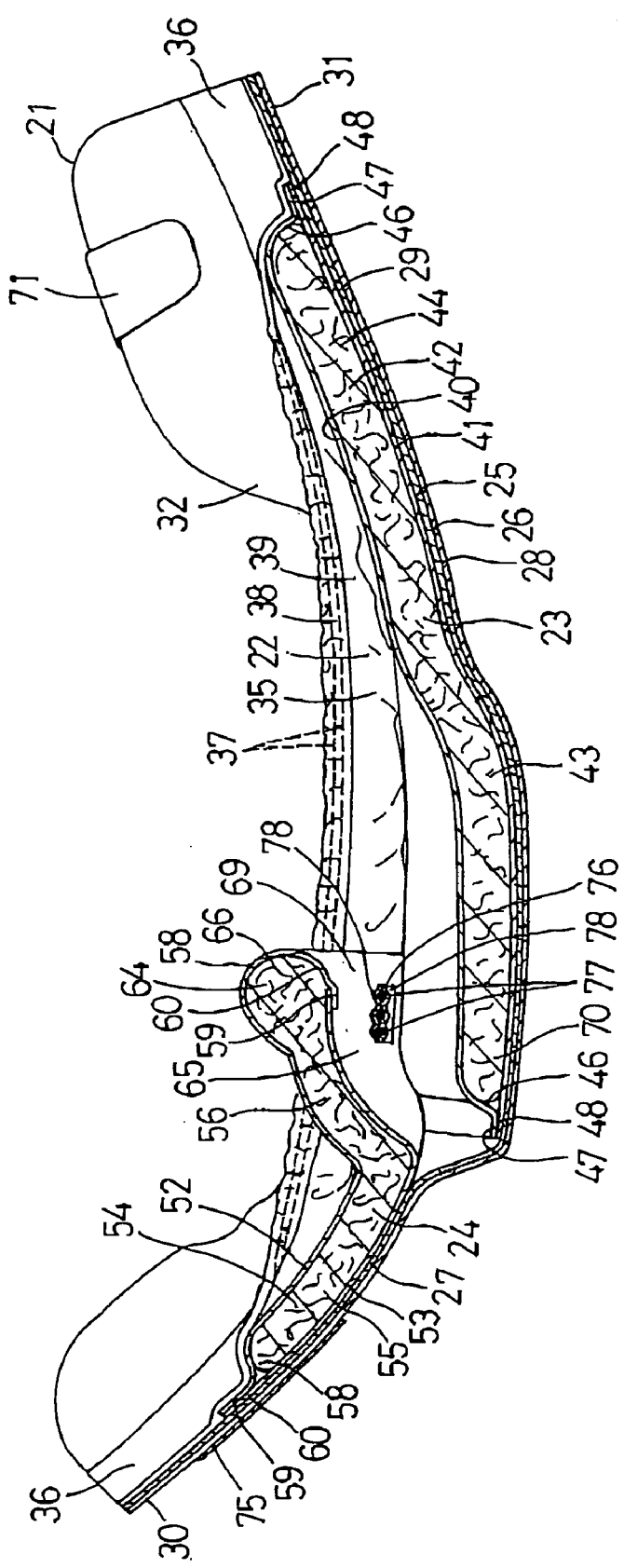
FIG. 15 is a sectional view taken along the line 15—15 in FIG. 13.
Figure 16:
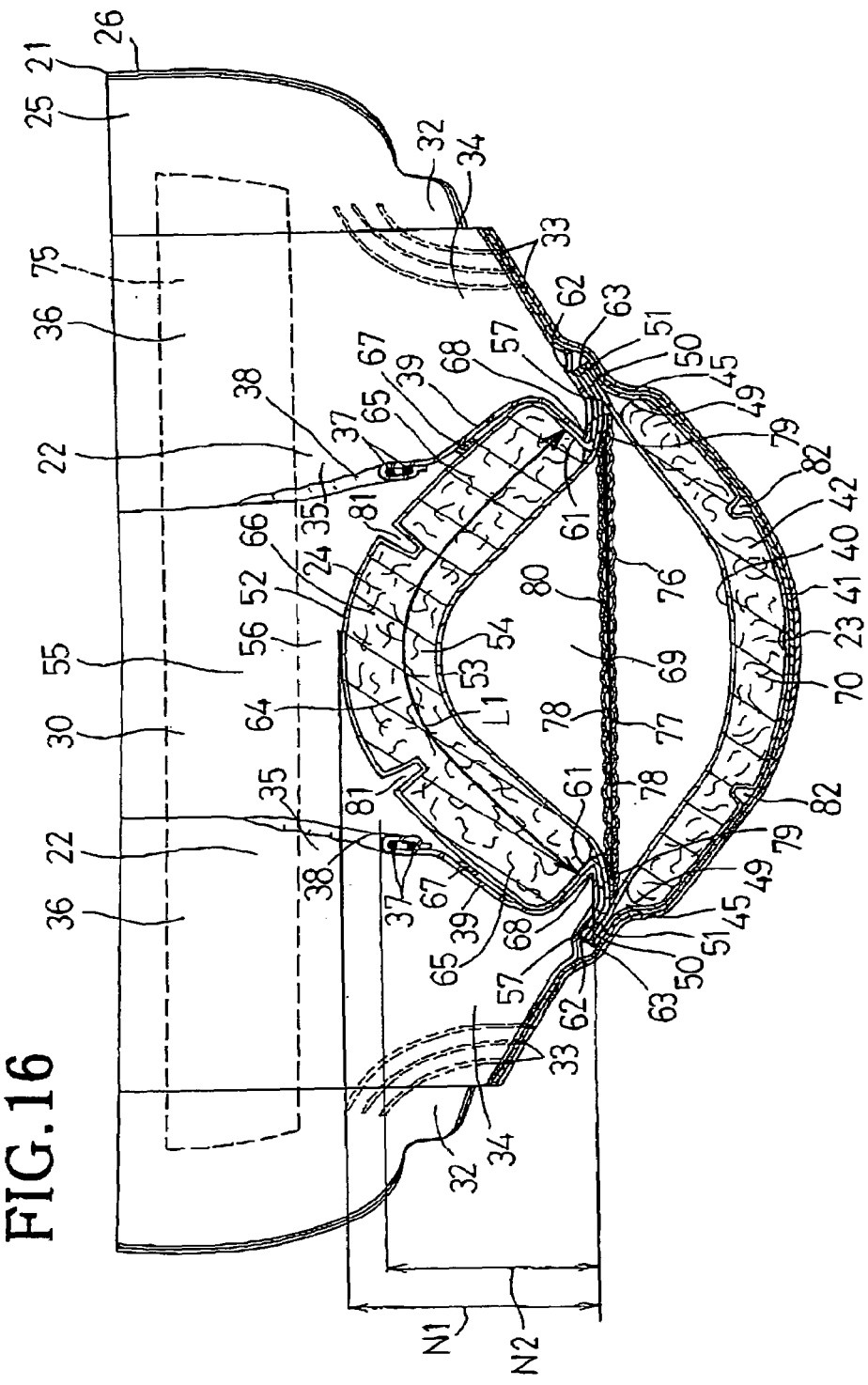
FIG. 16 is a sectional view taken along the line 16—16 in FIG. 13.

FIG. 13 is a perspective view showing a disposable wearing article 20D as further another embodiment of the invention, FIG. 14 is a partially cutaway plan view showing the article 20D of FIG. 13 as viewed from the side of first and second panels 23, 24, FIG. 15 is a sectional view taken along a line 15—15 in FIG. 13 and FIG. 16 is a sectional view taken along a line 16—16 in FIG. 13. In FIGS. 13 and 14, a transverse direction is indicated by an arrow L, a longitudinal direction is indicated by an arrow M and a thickness direction is indicated by an arrow N (in FIG. 13 alone). FIG. 14 shows the article 20D as developed against contractile force of elastic members 33, 37, 77 in the longitudinal direction as well as in the transverse direction.

This article 20D is similar to the article 20B of FIG. 5–8 except an arrangement such that the first panel 23 is further formed with folding guides 82 and, in the distal edge 64 of the distal portion 56, the side sections 65 as well as the transversely middle section 66 has a thickness dimension larger than that in the remaining region of the distal portion 56 except for the distal edge 64. The components similar to those in the article 20B of FIG. 5–8 are designated by the same reference numerals as those in FIG. 5–8 and the similar arrangements as those of the article 20B of FIG. 5–8 will not be repetitively described here.

The front portion 43 of the first panel 23 is formed with a pair of folding guides 82 extending in a generally longitudinal direction and spaced apart from each other by a predetermined dimension in the transverse direction. Specifically, these folding guides 82 extend to the transversely side edges 45 on the side of the rear portion 44, describing circular arcs which are convex inward as viewed in the transverse direction of the chassis 21 gradually increases from the front end 70 of the front portion 43 toward the rear portion 44. The transversely opposite side edges 45 are drawn inward as viewed in the transverse direction of the chassis 21 under the contractile force of the spacer 76. In response to this, the front portion 43 is folded along the respective folding guides 82 so that the front portion 43 is bent so as to describe a circular arc which is convex to a downward direction together with the chassis 21 in the thickness direction of the article 20D.

The core 42 along the folding guides 82 have a density and a basis weight less than those of the core 42 except for the folding guides 82. Correspondingly, the first panel 23 along these folding guides 82 present a stiffness lower than that presented by the first panel 24 except for the folding guides 82. An alternative arrangement is also possible such the folding guides 82 extend from terminate short of the transversely opposite fixed side edges 45.

The transversely middle section 66 of the distal portion 56 describes a circular arc which is convex upward above the side sections 65. The distal edge 64 of the distal portion 56 has a thickness dimension larger than a thickness dimension in the remaining region of the distal portion 56 except for the distal edge 64. The side sections 65 are partially joined to the intermediate sections 39 of the distal section 35 positioned aside toward the distal edges 38 of the respective leak-barrier sheets 22 in the vicinity of the folding guides 81.

The maximum height dimension N1 as measured from the lower end 68 of the distal section 35 of the leak-barrier sheet 22 to the transversely middle section 66 of the distal portion 56 is larger than the maximum height dimension N2 as measured from the lower end 68 to the distal edge 38 of the distal section 35 of the leak-barrier sheet 22. The transversely middle section 66 folded upward extends upward above the end portion 38 of the distal section 35 of the leak-barrier sheet 22. The distal edge 38, in turn, extends upward above the side section 65.

The front end 70 of the first panel 23 underlies the distal portion 56 of the second panel 24 and extends into the pocket 69. The front end 70 is bent so as to describe a circular arc which is convex to a downward direction together with the chassis 21 and thereby forms the pocket 69.

The front portion 43 of the first panel 23 is bent so as to describe a circular arc which is convex to a downward direction together with the chassis 21 so that, compared to the article 20A of FIG. 1, the article 20D can receive a larger amount of feces.

The distal edge 64 of the distal portion 56 has a thickness dimension larger than a thickness dimension of the region of the distal portion 56 except for the distal edge 64 and extends upward beyond the distal edge 38 of the distal sections 35 of the respective leak-barrier sheets 22. Such arrangement ensures that the transversely middle section 66 of the distal edge 64 reliably comes in close contact with the intermediate region defined between the genital organ and the anus of the wearer as the article 20D is put on the wearer's body and thereby forms the barrier adapted to divide the genital organ and the anus off from each other.

In any one of the articles 20B, 20C and 20D, the first and second panels 23, 24 may present a stiffness higher along the folding guides 81, 82 than a stiffness of these first and second panels 23, 24 except for the folding guides 81, 82. As an example of measures to establish such relationship in this alternative arrangement, the first and second panels 23, 24 may be compressed in the thickness direction along the folding guides 81, 82 and thereby increasing density of the cores 42, 54 along the folding guides 81, 82 maybe enhanced. In this case, the front portion 43 is folded along the folding guides 82 and the distal portion 56 is folded along the folding guides 81.

While the articles 20A, 20B, 20C and 20D are illustrated with the front portion 55 of the second panel 24 being joined to the front waist region 27 of the chassis 21, it is also possible that the front portion 55 is joined only to the front end 30 of the chassis 21. In this case, the pocket 69 is formed between a generally rear half of the front waist region 27 of the chassis 21 and a generally front half of the crotch region 28.

While the articles 20A, 20B, 20C and 20D are illustrated with transversely opposite side edges 57 of the second panel 24 being joined to the transversely opposite lateral sections 32 of the chassis 21, it is not essential that the opposite side edges 57 are joined over full extent thereof to the chassis 21. More specifically, at least segments of these side edges 57 extending along the distal edge 64 of the distal portion 56 may be joined to the lateral sections 32 of the chassis 21 to achieve the expected effect. In any one of the articles 20A, 20B, 20C and 20D, an alternative arrangement is possible such that the first panel 23 extends fully in the crotch region 28 as well as fully in the rear waist region 29.

Assumed that each of these articles 20A, 20B, 20C and 20D is divided by a transverse center line bisecting the longitudinal dimension thereof into front and rear halves and the front half is further divided by a transverse parting line into a middle section put aside toward the transverse center line and a distal section being remote from the transverse center line, the present invention can be effectively implemented so long as the distal portion 50 lies in this middle section of the articles 20A, 20B, 20C or 20D.

Stock materials for the liquid-pervious sheets 40, 52, 53 may be selected from the group consisting of a hydrophilic fibrous nonwoven fabric, hydrophobic fibrous nonwoven fabric having a plurality of perforations and a plastic film having a plurality of fine apertures. Stock materials for the leak-barrier sheets 22 and the liquid-impervious sheet 41 may be selected from the group consisting of a hydrophobic fibrous nonwoven fabric, a breathable liquid-impervious plastic film, a composite nonwoven fabric comprising two or more hydrophobic fibrous nonwoven fabric layers laminated one upon another and a composite sheet comprising a hydrophobic fibrous nonwoven fabric and a breathable liquid-impervious plastic film laminated upon each other. It is possible without departing from the scope of the invention to form the chassis 21, the leak-barrier sheets 22 and the liquid-impervious sheet 41 using a composite nonwoven fabric (SM nonwoven fabric, SMS nonwoven fabric or SMMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fibers selected from the group consisting of core-sheath conjugate fibers, side-by-side conjugate fibers, modified macaroni fibers, microporous fibers and fused type conjugate fibers.

The stretchable hydrophilic fibrous nonwoven fabric forming the water-pervious sheet may be of a melt blown nonwoven fabric or a spun bond nonwoven fabric. As component fiber for the stretchable fibrous nonwoven fabric, stretchable fibers obtained by a melt spinning thermoplastic elastomer resin. It is possible without departing from the scope of the invention to form the water-pervious sheet using a composite nonwoven fabric comprising a hydrophilic stretchable fibrous nonwoven fabric made of thermoplastic elastomer resin fibers and a hydrophilic fibrous nonwoven fabric made of crimped fibers obtained by a melt spinning thermoplastic synthetic resin selected from the group consisting of polypropylene, polyethylene and polyester laminated on at least one surface of the hydrophilic stretchable fibrous nonwoven fabric.

Each of the cores 42, 54 comprises a mixture of particulate or fibrous super-absorbent polymers and fluff pulp fibers or a mixture of a mixture of particulate or fibrous super-absorbent polymers, fluff pulp fibers and thermoplastic synthetic resin fibers, in any case, suitably compressed to a predetermined thickness dimension. Consequentially, the cores 42, 54 have a stiffness higher than that of the sheets. The cores 42, 54 are entirely wrapped with liquid-pervious sheets (not shown) such as tissue papers or hydrophilic fibrous nonwoven fabrics in order to prevent the cores 42, 54 from getting out of respective initial shapes thereof.

Joining of the sheets 22, 40, 41, 52, 53 to the chassis 21, joining of the sheets 40, 41, 52, 53 one to another, joining of the cores 42, 54 to the sheets 40, 41, 52, 53, and securing of the elastic members 33, 37, 77 to the sheet 22, 25, 26, 78 may be achieved by using adhesives or welding technique such as heat-sealing or sonic sealing. Adhesives may be selected from the group consisting of hot melt adhesive, acrylic adhesive, rubber-based adhesive and the like.

The adhesives are applied on the chassis 21, the leak-barrier sheets 22, the liquid-pervious sheets 40, 52, 53 and the liquid-impervious sheet 41 preferably in any one of spiral, wavy, zigzag, dotted or striped patterns. These chassis 21 and sheets 22, 40, 41, 52, 53 may be coated with adhesives in such patterns to define adhesive-coated regions and adhesive-free regions in these chassis 21 and sheets 22, 40, 41, 52, 53 and thereby to ensure that these chassis 21 and sheets 22, 40, 41, 52, 53 are intermittently joined one to another, the cores 42, 54 are intermittently and joined to the sheets 40, 41, 52, 53 and the elastic members 33, 37 are intermittently and joined to the sheet 22, 25, 26.

What is claimed is:

1. A disposable wearing article having longitudinal and transverse directions, said article comprising:
    a liquid-impervious chassis having a front waist region, a rear waist region, and a crotch region extending in the longitudinal direction between said front and rear waist regions;
    a pair of liquid-impervious leak-barrier sheets, wherein said leak-barrier sheets have
        proximal sections extending in the longitudinal direction along transversely opposite side edges of said chassis, respectively,
        distal sections provided with stretchable elastic members which extend in the longitudinal direction and are contractibly attached to said distal sections so that said distal sections are biased to rise above said chassis, and
        longitudinally opposite ends respectively bonded to the front and rear waist regions of said chassis and collapsed in the transverse direction;
    a body fluid absorbent first panel laid between said pair of leak-barrier sheets, joined to said chassis, and extending over said crotch region and said rear waist region of said chassis; and
    a body fluid absorbent second panel laid between said pair of leak-barrier sheets and extending over said front waist region and said crotch region of said chassis; wherein
    said second panel has
        a front portion joined to said front waist region of said chassis,
        a rear portion extending in said crotch region, and
        transversely opposite side edges extending in the longitudinal direction of said chassis; and
    said rear portion of said second panel has
        a pair of side sections extending upward from said chassis and being joined to the distal sections of said leak-barrier sheets, and
        a transversely middle section extending between said side sections so as to be convex upward above said side sections, said middle section at least partially extending upward beyond upper ends of said distal sections of the respective leak-barrier sheets, wherein said chassis and said rear portion of said second panel define therebetween a pocket open toward said rear region; and
    said side sections of said rear portion of said second panel are joined to said distal sections of said leak-barrier sheets at a level lower than said elastic members; and
    an absorbent core of said second panel includes a pair of folding guides which are spaced apart from each other by a predetermined distance in the transverse direction, extend in the longitudinal direction, and are formed between the side sections and the middle section in said rear portion of said second panel.

2. The wearing article defined by claim 1, wherein said distance between said folding guides gradually increases from said rear portion toward the front portion of said second panel.

3. The wearing article defined by claim 1, wherein said side sections of said rear portion of said second panel are joined to said distal sections of the respective leak-barrier sheets at a level below said folding guides.

4. The wearing article defined by claim 1, wherein said second panel has a lower stiffness along said folding guides than in areas of said rear portion of said second panel which are located outside said folding guides.

5. The wearing article defined by claim 1, wherein said second panel has a higher stiffness along said folding guides than in areas of said rear portion of said second panel which are located outside said folding guides.

6. The wearing article defined by claim 2, wherein said folding guides extend up to said transversely opposite side edges of said second panel.

7. A disposable wearing article having longitudinal and transverse directions, said article comprising:
   a liquid-impervious chassis having a front waist region, a rear waist region, and a crotch region extending in the longitudinal direction between said front and rear waist regions;
   a body fluid absorbent first panel joined to an upper side of said chassis and extending in the longitudinal direction from said rear waist region towards said front waist region; and
   a body fluid absorbent second panel comprising:
   a front portion joined to the upper side of said chassis in said front waist region, and
   a rear portion extending obliquely upwardly from the upper side of said chassis and rearwardly in the longitudinal direction from said front portion towards said rear waist region;
   wherein
   said second panel further comprises opposite upper and lower surfaces and an absorbent material between said upper and lower surfaces;
   the lower surface of said second panel in said rear portion is upwardly spaced from the upper side of said chassis to define a pocket between the lower surface of said second panel in said rear portion and the upper side of said chassis, said pocket being open rearwardly in the longitudinal direction towards said rear waist region;
   said article further comprises a pair of liquid-impervious leak-barrier sheets between which said first and second panels are positioned, wherein each of said leak-barrier sheets has
   a proximal section extending in the longitudinal direction along one of transversely opposite side edges of said chassis, said proximal section being attached to the upper side of said chassis; and
   a distal section having a stretchable elastic member contractibly attached thereto so as to bias said distal section to rise above said chassis;
   the upper surface of said second panel in said rear portion is bonded to each of said leak-barrier sheets at a location situated between the elastic member and the proximal section of said leak-barrier sheet;
   a pair of folding guides spaced apart from each other by a predetermined distance in the transverse direction and extending in the longitudinal direction are formed in said rear portion of said second panel; and
   the locations at which the upper surface of said second panel in said rear portion is bonded to said leak-barrier sheets are situated below said folding guides.

8. A disposable wearing article having longitudinal and transverse directions, said article comprising:
   a liquid-impervious chassis having a front waist region, a rear waist region, and a crotch region extending in the longitudinal direction between said front and rear waist regions;
   a body fluid absorbent first panel joined to an upper side of said chassis and extending in the longitudinal direction from said rear waist region towards said front waist region; and
   a body fluid absorbent second panel comprising:
   a front portion joined to the upper side of said chassis in said front waist region, and
   a rear portion extending obliquely upwardly from the upper side of said chassis and rearwardly in the longitudinal direction from said front portion towards said rear waist region;
   wherein
   said second panel further comprises opposite upper and lower surfaces and an absorbent material between said upper and lower surfaces;
   the lower surface of said second panel in said rear portion is upwardly spaced from the upper side of said chassis to define a pocket between the lower surface of said second panel in said rear portion and the upper side of said chassis, said pocket being open rearwardly in the longitudinal direction towards said rear waist region;
   a pair of folding guides spaced apart from each other by a predetermined distance in the transverse direction and extending in the longitudinal direction are formed in said rear portion of said second panel; and
   said distance between said folding guides gradually increases from said rear portion toward the front portion of said second panel.

* * * * *